(12) United States Patent
Liang et al.

(10) Patent No.: US 8,318,922 B2
(45) Date of Patent: Nov. 27, 2012

(54) TREATMENT AND PREVENTION OF HYPERPROLIFERATIVE CONDITIONS IN HUMANS AND ANTISENSE OLIGONUCLEOTIDE INHIBITION OF HUMAN REPLICATION-INITIATION PROTEINS

(75) Inventors: Chun Liang, Hong Kong (CN); Dao-rong Feng, Hong Kong (CN); Zhi-ling Yu, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 136 days.

(21) Appl. No.: 12/126,862

(22) Filed: May 24, 2008

(65) Prior Publication Data

US 2008/0300212 A1    Dec. 4, 2008

Related U.S. Application Data

(63) Continuation-in-part of application No. 10/232,923, filed on Aug. 29, 2002, now Pat. No. 7,393,950.

(51) Int. Cl.
  *C07H 21/00*    (2006.01)
  *C07H 21/02*    (2006.01)
  *C07H 2/04*    (2006.01)
(52) U.S. Cl. ...................... 536/24.5; 536/23.1; 536/24.3
(58) Field of Classification Search ........................ None
  See application file for complete search history.

(56) References Cited

U.S. PATENT DOCUMENTS

| | | | | |
|---|---|---|---|---|
| 4,394,443 | A * | 7/1983 | Weissman et al. | 435/6 |
| 6,107,091 | A * | 8/2000 | Cowsert | 435/375 |
| 7,022,828 | B2 * | 4/2006 | McSwiggen | 536/23.1 |
| 2003/0082546 | A1 * | 5/2003 | Ashkenazi et al. | 435/6 |
| 2005/0261212 | A1 * | 11/2005 | McSwiggen | 514/44 |

OTHER PUBLICATIONS

Cohen, J. (1992) Selective Anti-Gene Therapy for Cancer: Principles and Prospects, Tohoku J. Exp. Med., v.168:351-9.*

* cited by examiner

*Primary Examiner* — Jennifer Pitrak McDonald
(74) *Attorney, Agent, or Firm* — Duane Morris LLP; Siegfried J. W. Ruppert

(57) ABSTRACT

Antisense oligonucleotides that inhibit expression of human replication-initiation protein as well as methods of preventing or treating hyperproliferative conditions using said oligonucleotides are disclosed. One aspect provides an antisense oligonucleotide that inhibits the expression of human replication-initiation protein and has a sequence complementary to at least a portion of a target sequence encoding a human replication-initiation gene. By administering a therapeutically effective amount of an antisense oligonucleotide or by contacting the hyperproliferating cells with an effective amount of one or more antisense oligonucleotides, expression of replication-initiation protein is inhibited. Methods of screening and testing active antisense oligonucleotides for their ability to inhibit gene expression are also disclosed.

1 Claim, 9 Drawing Sheets

```
                           SEQUENCE LISTING

<160> NUMBER OF SEQ ID NOS: 30

<210> SEQ ID NO 1
<211> LENGTH: 16
<212> TYPE: DNA
<213> ORGANISM: Artificial Sequence
<220> FEATURE:
<223> OTHER INFORMATION: Oligonucleotide

<400> SEQUENCE: 1
aaggtgggaa gttcaa                                                       16

<210> SEQ ID NO 2
<211> LENGTH: 16
<212> TYPE: DNA
<213> ORGANISM: Artificial Sequence
<220> FEATURE:
<223> OTHER INFORMATION: Oligonucleotide

<400> SEQUENCE: 2
aagatgggta ggtcaa                                                       16

<210> SEQ ID NO 3
<211> LENGTH: 16
<212> TYPE: DNA
<213> ORGANISM: Artificial Sequence
<220> FEATURE:
<223> OTHER INFORMATION: Oligonucleotide

<400> SEQUENCE: 3
ttgaacttcc cacctt                                                       16
```

```
<210> SEQ ID NO 4
<211> LENGTH: 18
<212> TYPE: DNA
<213> ORGANISM: Artificial Sequence
<220> FEATURE:
<223> OTHER INFORMATION: Oligonucleotide

<400> SEQUENCE: 4
ctccctcttg gctcaagg                                                 18

<210> SEQ ID NO 5
<211> LENGTH: 18
<212> TYPE: DNA
<213> ORGANISM: Artificial Sequence
<220> FEATURE:
<223> OTHER INFORMATION: Oligonucleotide

<400> SEQUENCE: 5
ctcccacctg gttctagg                                                 18

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide

<400> SEQUENCE: 6
ccttgagcca agagggag                                                 18

<210> SEQ ID NO 7
<211> LENGTH: 19
<212> TYPE: DNA
<213> ORGANISM: Artificial Sequence
<220> FEATURE:
<223> OTHER INFORMATION: Oligonucleotide

<400> SEQUENCE: 7
agcctggcca acatggtaa                                                19

<210> SEQ ID NO 8
<211> LENGTH: 19
<212> TYPE: DNA
<213> ORGANISM: Artificial Sequence
<220> FEATURE:
<223> OTHER INFORMATION: Oligonucleotide

<400> SEQUENCE: 8
agccggacca gcattgtaa                                                19

<210> SEQ ID NO 9
<211> LENGTH: 19
<212> TYPE: DNA
<213> ORGANISM: Artificial Sequence
<220> FEATURE:
<223> OTHER INFORMATION: Oligonucleotide

<400> SEQUENCE: 9
ttaccatgtt ggccaggct                                                19

<210> SEQ ID NO 10
<211> LENGTH: 16
<212> TYPE: DNA
<213> ORGANISM: Artificial Sequence
<220> FEATURE:
<223> OTHER INFORMATION: Oligonucleotide
```

```
<400> SEQUENCE: 10
cttgaagacg ttgtgg                                                     16

<210> SEQ ID NO 11
<211> LENGTH: 16
<212> TYPE: DNA
<213> ORGANISM: Artificial Sequence
<220> FEATURE:
<223> OTHER INFORMATION: Oligonucleotide

<400> SEQUENCE: 11
ctttaaggcg tagtgg                                                     16

<210> SEQ ID NO 12
<211> LENGTH: 16
<212> TYPE: DNA
<213> ORGANISM: Artificial Sequence
<220> FEATURE:
<223> OTHER INFORMATION: Oligonucleotide

<400> SEQUENCE: 12
ccacaacgtc ttcaag                                                     16

<210> SEQ ID NO 13
<211> LENGTH: 16
<212> TYPE: DNA
<213> ORGANISM: Artificial Sequence
<220> FEATURE:
<223> OTHER INFORMATION: Oligonucleotide

<400> SEQUENCE: 13
cagaaccagg gcccca                                                     16

<210> SEQ ID NO 14
<211> LENGTH: 16
<212> TYPE: DNA
<213> ORGANISM: Artificial Sequence
<220> FEATURE:
<223> OTHER INFORMATION: Oligonucleotide

<400> SEQUENCE: 14
cagcagcagg ccacca                                                     16

<210> SEQ ID NO 15
<211> LENGTH: 16
<212> TYPE: DNA
<213> ORGANISM: Artificial Sequence
<220> FEATURE:
<223> OTHER INFORMATION: Oligonucleotide

<400> SEQUENCE: 15
tggggccctg gttctg                                                     16

<210> SEQ ID NO 16
<211> LENGTH: 17
<212> TYPE: DNA
<213> ORGANISM: Artificial Sequence
<220> FEATURE:
<223> OTHER INFORMATION: Oligonucleotide

<400> SEQUENCE: 16
tcccgcagat ggatgcg                                                    17

<210> SEQ ID NO 17
<211> LENGTH: 17
```

```
<212> TYPE: DNA
<213> ORGANISM: Artificial Sequence
<220> FEATURE:
<223> OTHER INFORMATION: Oligonucleotide

<400> SEQUENCE: 17
tccctcaggt ggaagcc                                                   17

<210> SEQ ID NO 18
<211> LENGTH: 17
<212> TYPE: DNA
<213> ORGANISM: Artificial Sequence
<220> FEATURE:
<223> OTHER INFORMATION: Oligonucleotide

<400> SEQUENCE: 18
cgcatccatc tgcggga                                                   17

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide

<400> SEQUENCE: 19
aggctgtcat ggagggacca                                                20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide

<400> SEQUENCE: 20
aggctctgag ggagtgagca                                                20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide

<400> SEQUENCE: 21
tggtccctcc atgacagcct                                                20

<210> SEQ ID NO 22
<211> LENGTH: 19
<212> TYPE: DNA
<213> ORGANISM: Artificial Sequence
<220> FEATURE:
<223> OTHER INFORMATION: Oligonucleotide

<400> SEQUENCE: 22
cccgcatgtc cttcatccc                                                 19

<210> SEQ ID NO 23
<211> LENGTH: 19
<212> TYPE: DNA
<213> ORGANISM: Artificial Sequence
<220> FEATURE:
<223> OTHER INFORMATION: Oligonucleotide

<400> SEQUENCE: 23
cgcgtatgcc catcttccc                                                 19
```

```
<210> SEQ ID NO 24
<211> LENGTH: 19
<212> TYPE: DNA
<213> ORGANISM: Artificial Sequence
<220> FEATURE:
<223> OTHER INFORMATION: Oligonucleotide

<400> SEQUENCE: 24
gggatgaagg acatgcgcg                                                   19

<210> SEQ ID NO 25
<211> LENGTH: 16
<212> TYPE: DNA
<213> ORGANISM: Artificial Sequence
<220> FEATURE:
<223> OTHER INFORMATION: Oligonucleotide

<400> SEQUENCE: 25
gaagtgatct gtccct                                                      16

<210> SEQ ID NO 26
<211> LENGTH: 16
<212> TYPE: DNA
<213> ORGANISM: Artificial Sequence
<220> FEATURE:
<223> OTHER INFORMATION: Oligonucleotide

<400> SEQUENCE: 26
gaggtgaact ttccct                                                      16

<210> SEQ ID NO 27
<211> LENGTH: 16
<212> TYPE: DNA
<213> ORGANISM: Artificial Sequence
<220> FEATURE:
<223> OTHER INFORMATION: Oligonucleotide

<400> SEQUENCE: 27
agggagagat cacttc                                                      16

<210> SEQ ID NO 28
<211> LENGTH: 3053
<212> TYPE: DNA
<213> ORGANISM: Homo sapiens

<400> SEQUENCE: 28
gagcgcggct ggagtttgct gctgccgctg tgcagtttgt tcagggggctt gtggtggtga      60 gtccgagagg ctgcgtgtga gagacgtgag aaggatcctg cactgaggag gtggaaagaa     120
gaggattgct cgaggaggcc tggggtctgt gaggcagcgg agctgggtga aggctgcggg     180
ttccggcgag gcctgagctg tgctgtcgtc atgcctcaaa cccgatccca ggcacaggct     240
acaatcagtt ttccaaaaag gaagctgtct cgggcattga acaaagctaa aaactccagt     300
gatgccaaac tagaaccaac aaatgtccaa accgtaacct gttctcctcg tgtaaaagcc     360
ctgcctctca gccccaggaa acgtctgggc gatgacaacc tatgcaacac tcccatttta     420
cctccttgtt ctccaccaaa gcaaggcaag aaagagaatg gtccccctca ctcacataca     480
cttaagggac gaagattggt atttgacaat cagctgacaa ttagtctcc tagcaaaaga     540 gaactagcca agttcaccc aaacaaaata ctttcttcag ttagaaaaag tcaagagatc     600
acaacaaatt ctgagcagag atgtccactg aagaaagat ctgcatgtgt gagactattc      660
aagcaagaag gcacttgcta ccagcaagca aagctggtcc tgaacacagc tgtcccagat     720
```

```
cggctgcctg ccagggaaag ggagatggat gtcatcagga atttcttgag ggaacacatc    780
tgtgggaaaa aagctggaag cctttacctt tctggtgctc ctggaactgg aaaaactgcc    840
tgcttaagcc ggattctgca agacctcaag aaggaactga aaggctttaa aactatcatg    900
ctgaattgca tgtccttgag gactgcccag gctgtattcc cagctattgc tcaggagatt    960
tgtcaggaag aggtatccag gccagctggg aaggacatga tgaggaaatt ggaaaaacat   1020
atgactgcag agaagggccc catgattgtg ttggtattgg acgagatgga tcaactggac   1080
agcaaaggcc aggatgtatt gtacacgcta tttgaatggc catggctaag caattctcac   1140
ttggtgctga ttggtattgc taatacctg atctcacag atagaattct acctaggctt    1200
caagctagag aaaatgtaa gccacagctg ttgaacttcc caccttatac cagaaatcag    1260
atagtcacta ttttgcaaga tcgacttaat caggtatcta gagatcaggt tctggacaat   1320
gctgcagttc aattctgtgc ccgcaaagtc tctgctgttt caggagatgt tcgcaaagca   1380
ctggatgttt gcaggagagc tattgaaatt gtagagtcag atgtcaaaag ccagactatt   1440
ctcaaaccac tgtctgaatg taaatcacct tctgagcctc tgattcccaa gagggttggt   1500
cttattcaca tatcccaagt catctcagaa gttgatggta acaggatgac cttgagccaa   1560
gaaggagcac aagattcctt ccctcttcag cagaagatct tggtttgctc tttgatgctc   1620
ttgatcaggc agttgaaaat caagaggtc actctgggga agttatatga agcctacagt   1680
aaagtctgtc gcaaacagca ggtggcggct gtggaccagt cagagtgttt gtcactttca   1740
gggctcttgg aagccagggg cattttagga ttaaagagaa acaaggaaac ccgtttgaca   1800
aaggtgtttt tcaagattga agagaaagaa atagaacatg ctctgaaaga taaagcttta   1860
attggaaata tcttagctac tggattgcct taaattcttc tcttacaccc cacccgaaag   1920
tattcagctg gcatttagag agctacagtc ttcatttag tgctttacac attcgggcct   1980
gaaaacaaat atgacctttt ttacttgaag ccaatgaatt ttaatctata gattcttaa    2040
tattagcaca gaataatatc tttgggtctt actattttta cccataaaag tgaccaggta   2100
gaccctttt aattacattc actacttcta ccacttgtgt atctctagcc aatgtgcttg    2160
caagtgtaca gatctgtgta gaggaatgtg tgtatattta cctcttcgtt tgctcaaaca   2220
tgagtgggta tttttttgtt tgtttttttt gttgttgttg ttttgagggc gcgtctcacc   2280
ctgttgccca ggctggagtg caatggcgcg ttctctgctc actacagcac ccgcttccca   2340
ggttgaagtg attctcttgc ctcagcctcc cgagtagctg ggattacagg tgcccaccac   2400
cgcgcccagc taattttta attttagta gagacagggt tttaccatgt tggccaggct    2460
ggtcttgaac tcctgaccct caagtgatct gcccaccttg gcctcctaa gtgctgggat    2520
tataggcgtg agccaccatg ctcagccatt aaggtatttt gttaagaact ttaagtttag   2580
ggtaagaaga atgaaaatga tccagaaaaa tgcaagcaag tccacatgga gatttggagg   2640
acactggtta aagaatttat ttctttgtat agtatactat gttcatggtg cagatactac   2700
aacattgtgg catttagac tcgttgagtt tcttgggcac tcccaagggc gttggggtca    2760
taaggagact ataactctac agattgtgaa tatatttatt ttcaagttgc attctttgtc   2820
tttttaagca atcagattc aagagagctc aagctttcag aagtcaatgt gaaaattcct    2880
tcctaggctg tcccacagtc tttgctgccc ttagatgaag ccacttgttt caagatgact   2940
actttggggt tgggttttca tctaaacaca ttttccagt cttattagat aaattagtcc    3000
atatggttgg ttaatcaaga gccttctggg tttggtttgg tggcattaaa tgg           3053
```

<210> SEQ ID NO 29
<211> LENGTH: 1938
<212> TYPE: DNA
<213> ORGANISM: Homo sapiens

<400> SEQUENCE: 29

| | | | | | |
|---|---|---|---|---|---|
| gatttggcgg | gagtcttgac | cgccgccggg | ctcttggtac | ctcagcgcga | gcgccaggcg | 60 |
| tccggccgcc | gtggctatgt | tcgtgtccga | tttccgcaaa | gagttctacg | aggtggtcca | 120 |
| gagccagagg | gtccttctct | tcgtggcctc | ggacgtggat | gctctgtgtg | cgtgcaagat | 180 |
| ccttcaggcc | ttgttccagt | gtgaccacgt | gcaatatacg | ctggttccag | tttctgggtg | 240 |
| gcaagaactt | gaaactgcat | tcttgagca | taaagaacag | tttcattatt | ttattctcat | 300 |
| aaactgtgga | gctaatgtag | acctattgga | tattcttcaa | cctgatgaag | acactatatt | 360 |
| ctttgtgtgt | gacacccata | ggccagtcaa | tgtcgtcaat | gtatacaacg | atacccagat | 420 |
| caaattactc | attaaacaag | atgatgacct | tgaagttccc | gcctatgaag | acatcttcag | 480 |
| ggatgaagag | gaggatgaag | agcattcagg | aaatgacagt | gatgggtcag | agccttctga | 540 |
| gaagcgcaca | cggttagaag | aggagatagt | ggagcaaacc | atgcggagga | ggcagcggcg | 600 |
| agagtgggag | gcccggagaa | gagacatcct | ctttgactac | gagcagtatg | aatatcatgg | 660 |
| gacatcgtca | gccatggtga | tgtttgagct | ggcttggatg | ctgtccaagg | acctgaatga | 720 |
| catgctgtgg | tgggccatcg | ttggactaac | agaccagtgg | gtgcaagaca | agatcactca | 780 |
| aatgaaatac | gtgactgatg | ttggtgtcct | gcagcgccac | gtttcccgcc | acaaccaccg | 840 |
| gaacgaggat | gaggagaaca | cactctccgt | ggactgcaca | cggatctcct | tgagtatga | 900 |
| cctccgcctg | gtgctctacc | agcactggtc | cctccatgac | agcctgtgca | acaccagcta | 960 |
| taccgcagcc | aggttcaagc | tgtggtctgt | gcatggacag | aagcggctcc | aggagttcct | 1020 |
| tgcagacatg | ggtcttcccc | tgaagcaggt | gaagcagaag | ttccaggcca | tggacatctc | 1080 |
| cttgaaggag | aatttgcggg | aaatgattga | agagtctgca | aataaatttg | ggatgaagga | 1140 |
| catgcgcgtg | cagactttca | gcattcattt | tgggttcaag | cacaagtttc | tggccagcga | 1200 |
| cgtggtcttt | gccaccatgt | ctttgatgga | gagccccgag | aaggatggct | cagggacaga | 1260 |
| tcacttcatc | caggctctgg | acagcctctc | caggagtaac | ctggacaagc | tgtaccatgg | 1320 |
| cctggaactc | gccaagaagc | agctgcgagc | cacccagcag | accattgcca | gctgcctttg | 1380 |
| caccaacctc | gtcatctccc | aggggccttt | cctgtactgc | tctctcatgg | agggcactcc | 1440 |
| agatgtcatg | ctgttctcta | ggccggcatc | cctaagcctg | ctcagcaaac | acctgctcaa | 1500 |
| gtcctttgtg | tgttcgacaa | agaaccggcg | ctgcaaactg | ctgccctgg | tgatggctgc | 1560 |
| ccccctgagc | atggagcatg | gcacagtgac | cgtggtgggc | atcccccag | agaccgacag | 1620 |
| ctcggacagg | aagaactttt | tggggagggc | gtttgagaag | gcagcggaaa | gcaccagctc | 1680 |
| ccggatgctg | cacaaccatt | tgacctctc | agtaattgag | ctgaaagctg | aggatcggag | 1740 |
| caagtttctg | gacgcactta | tttccctcct | gtcctaggaa | tttgattctt | ccagaatgac | 1800 |
| cttcttattt | atgtaactgg | ctttcattta | gattgtaagt | tatggacatg | atttgagatg | 1860 |
| tagaagccat | tttttattaa | ataaaatgct | tattttaggc | tccgtcccca | aaaaaaaaa | 1920 |
| aaaaaaaaaa | aaaaaaaa | | | | | 1938 |

<210> SEQ ID NO 30
<211> LENGTH: 3431
<212> TYPE: DNA
<213> ORGANISM: Homo sapien

<400> SEQUENCE: 30

```
gttgttgctg tagtggcgga gaggatcgtg gtactgctat ggcggaatca tcggaatcct      60
tcaccatggc atccagcccg gcccagcgtc ggcgaggcaa tgatcctctc acctccagcc     120
ctggccgaag ctcccggcgt actgatgccc tcacctccag ccctggccgt gaccttccac     180
catttgagga tgagtccgag gggctcctag gcacagaggg gcccctggag aagaagagg      240
atggagagga gctcattgga gatggcatgg aaagggacta ccgcgccatc ccagagctgg     300
acgcctatga ggccgaggga ctggctctgg atgatgagga cgtagaggag ctgacggcca     360
gtcagaggga ggcagcagag cgggccatgc ggcagcgtga ccgggaggct ggccggggcc     420
tgggccgcat gcgccgtggg ctcctgtatg acagcgatga ggaggacgag gagcgccctg     480
cccgcaagcg ccgccaggtg gagcgggcca cggaggacgg cgaggaggac gaggagatga     540
ttgagagcat cgagaacctg gaggatctca aaggccactc tgtgcgcgag tgggtgagca     600
tggcgggccc ccggctggag atccaccacc gcttcaagaa cttcctgcgc actcacgtcg     660
acagccacgg ccacaacgtc ttcaaggagc gcatcagcga catgtgcaaa gagaaccgtg     720
agagcctggt ggtgaactat gaggacttgg cagccaggga gcacgtgctg cctacttcc      780
tgcctgaggc accggcggag ctgctgcaga tctttgatga ggctgccctg gaggtggtac     840
tggccatgta ccccaagtac gaccgcatca ccaaccacat ccatgtccgc atctcccacc     900
tgcctctggt ggaggagctg cgctcgctga ggcagctgca tctgaaccag ctgatccgca     960
ccagtggggt ggtgaccagc tgcactggcg tcctgcccca gctcagcatg gtcaagtaca    1020
actgcaacaa gtgcaatttc gtcctgggtc ctttctgcca gtcccagaac caggaggtga    1080
aaccaggctc ctgtcctgag tgccagtcgg ccggccctt tgaggtcaac atggaggaga     1140
ccatctatca gaactaccag cgtatccgaa tccaggagag tccaggcaaa gtggcggctg    1200
gccggctgcc ccgctccaag gacgccattc tcctcgcaga tctggtggac agctgcaagc    1260
caggagacga gatagagctg actggcatct atcacaacaa ctatgatggc tccctcaaca    1320
ctgccaatgg cttccctgtc tttgccactg tcatcctagc caaccacgtg ccaagaagg     1380
acaacaaggt tgctgtaggg gaactgaccg atgaagatgt gaagatgatc actagcctct    1440
ccaaggatca gcagatcgga gagaaagatc ttgccagcat tgctccttcc atctatggtc    1500
atgaagacat caagagaggc ctggctctgg ccctgttcag aggggagccc aaaaacccag    1560
gtggcaagca caaggtacgt ggtgatatca acgtgctctt gtgcggagac cctggcacag    1620
cgaagtcgca gtttctcaag tatattgaga aagtgtccag ccgagccatc ttcaccactg    1680
gccaggggc gtcggctgtg ggcctcacgg cgtatgtcca gcggcaccct gtcagcaggg     1740
agtggacctt ggaggctggg gccctggttc tggctgaccg aggagtgtgt ctcattgatg    1800
aatttgacaa gatgaatgac caggacagaa ccagcatcca tgaggccatg gagcaacaga    1860
gcatctccat ctcgaaggct ggcatcgtca cctccctgca ggctcgctgc acggtcattg    1920
ctgccgccaa ccccatagga gggcgctacg accctcgct gactttctct gagaacgtgg     1980
acctcacaga gcccatcatc tcacgctttg acatcctgtg tgtggtgagg gacaccgtgg    2040
acccagtcca ggacgagatg ctggcccgct tcgtggtggg cagccacgtc agacaccacc    2100
ccagcaacaa ggaggaggag gggctggcca atggcagcgc tgctgagccc gccatgccca    2160
acacgtatgg cgtggagccc ctgccccagg aggtcctgaa gaagtacatc atctacgcca    2220
aggagagggt ccacccgaag ctcaaccaga tggaccagga caaggtggcc aagatgtaca    2280
gtgacctgag gaaagaatct atggcgacag gcagcatccc cattacggtg cggcacatcg    2340
```

```
agtccatgat ccgcatggcg gaggcccacg cgcgcatcca tctgcgggac tatgtgatcg    2400
aagacgacgt caacatggcc atccgcgtga tgctggagag cttcatagac acacagaagt    2460
tcagcgtcat gcgcagcatg cgcaagactt tgcccgcta cctttcattc ggcgtgaca      2520
acaatgagct gttgctcttc atactgaagc agttagtggc agagcaggtg acatatcagc    2580
gcaaccgctt tggggcccag caggacacta ttgaggtccc tgagaaggac ttggtggata    2640
aggctcgtca gatcaacatc cacaacctct ctgcatttta tgacagtgag ctcttcagga    2700
tgaacaagtt cagccacgac ctgaaaagga aaatgatcct gcagcagttc tgaggcccta    2760
tgccatccat aaggattcct tgggattctg gtttggggtg gtcagtgccc tctgtgcttt    2820
atggacacaa aaccagagca cttgatgaac tcggggtact agggtcaggg cttatagcag    2880
gatgtctggc tgcacctggc atgactgttt gtttctccaa gcctgctttg tgcttctcac    2940
ctttgggtgg gatgccttgc cagtgtgtct tacttggttg ctgaacatct tgccacctcc    3000
gagtgctttg tctccactca gtaccttgga tcagagctgc tgagttcagg atgcctgcgt    3060
gtggtttagg tgttagcctt cttacatgga tgtcaggaga gctgctgccc tcttggcgtg    3120
agttgcgtat tcaggctgct tttgctgcct ttggccagag agctggttga agatgtttgt    3180
aatcgttttc agtctcctgc aggtttctgt gccctgtgg tggaagaggg cacgacagtg     3240
ccagcgcagc gttctgggct cctcagtcgc aggggtggga tgtgagtcat gcggattatc    3300
cactcgccac agttatcagc tgccattgct ccctgtctgt ttccccactc tcttatttgt    3360
gcattcggtt tggtttctgt agttttaatt tttaataaag ttgaataaaa tataaaaaaa    3420
aaaaaaaaa a                                                          3431
```

TREATMENT AND PREVENTION OF HYPERPROLIFERATIVE CONDITIONS IN HUMANS AND ANTISENSE OLIGONUCLEOTIDE INHIBITION OF HUMAN REPLICATION-INITIATION PROTEINS

CROSS-REFERENCE TO RELATED APPLICATIONS

This is a continuation-in-part of application Ser. No. 10/232,923, filed on Aug. 29, 2002, incorporated herein by reference.

REFERENCE TO SEQUENCE LISTING

An electronic copy of the "Sequence Listing" in computer readable form in compliance with 37 C.F.R. §1.821 to 1.825 is submitted herewith. The sequence listing information in computer readable form is identical to the paper sequence listing enclosed and incorporated herein by reference.

BACKGROUND

The present invention relates to treatment and prevention of hyperproliferative conditions in humans and more particularly to antisense oligonucleotides complementary to human replication-initiation genes which modulate DNA replication and cell proliferation. This invention also relates to methods of using such oligonucleotides to inhibit the growth of tumor cells in mammals.

Cancer presents one of the most serious threats to human health and life. There are approximately ten million new cancer cases and seven million cancer-related deaths every year in the world. In fact, approximately one in every four people has the probability of developing cancer during their lifetime.

Some examples of anticancer drugs currently available are cytotoxins, DNA damaging agents, and inhibitors of oncogenic proteins involved in signal transduction pathways for cell proliferation. However, few of the current anticancer drugs are effective or without side effects. Many of these drugs are not highly selective towards cancer cells and these drugs also damage normal cells or inhibit the metabolism and cellular functions of normal cells. Moreover, most oncogenic signal transduction pathways are redundant in the cells, therefore treatments that block individual pathways can be bypassed by cancer cells and inhibition of one or some of these pathways may not stop cancer growth.

Antisense oligonucleotides are known to be able to inhibit gene expression, and have been used in combination with chemotherapeutic agents to develop anticancer strategies in mouse xenographs (Geiger, T. et al., Anti-Cancer Drug Design, 13, 35-45 (1998), Del Bufalo, D. et al, British J. of Cancer, 74, 387-393 (1996)). Current theories suggest that the activity of antisense oligonucleotides depends on the binding of the oligonucleotides to the target nucleic acid (e.g. to at least a portion of a genomic region, gene or mRNA transcript thereof), thus disrupting the function of the target, either by hybridization arrest or by destruction of target RNA by RNase H (activated by nucleotide hybridization to RNA). For example, antisense oligonucleotides bind to the complementary sequence on a target mRNA nucleic acid sequence, thus activating endogenous RNase H to cleave mRNA. Binding of antisense oligonucleotides to mRNA may also interfere with translation thereby reducing or eliminating production of a gene even if the mRNA is not degraded (Milligan, J. F., et al, J. Med. Chem., 36, 1923-1927 (1993)). However, known antisense oligonucleotides have not targeted human replication-initiation genes, nor demonstrated any efficacy in inhibiting expression of replication-initiation proteins in human cells.

Proteins involved in the initiation of DNA replication (i.e., genome duplication) present excellent targets for cancer therapy. Initiation of DNA replication is controlled by the cis-acting DNA elements called replicators and the trans-acting initiation proteins that interact with the replicators. To date, several groups of initiation proteins required for eukaryotic DNA replication have been identified. These include ORC (origin recognition complex), Cdc6 (cell division cycle), MCM (minichromosome maintenance), Cdc45 and Cdt1 proteins (Takisawa, H., et al., Curr. Opin. Cell. Biol. 12, 690-696 (2000)). ORC binds chromatin throughout the cell cycle, whereas the chromatin association of other groups is cell cycle-regulated (Leatherwood, J., Curr. Opin. Cell. Biol., 10, 742-748 (1998)). Some of the initiation proteins in humans, such as Cdc6 and MCM proteins, are expressed in cancerous, but not in normal, non-dividing cells (Williams, G. H. et al., Proc. Natl. Acad. Sci. USA, 95, 14932-14937 (1998)). Gene sequences encoding some of these proteins have been isolated (Williams, U.S. Pat. No. 5,851,821; Saha, P. et al., J. Biol. Chem., 50, 6075-6086 (1990); Todorov, L T., et al., J. Cell Sci., 107, 253-265 (1994)).

SUMMARY

The present invention relates to treatment and prevention of hyperproliferative conditions in humans and to antisense oligonucleotides that inhibit expression of human replication-initiation protein as well as methods of preventing or treating hyperproliferative conditions using these oligonucleotides. Methods of screening and testing active antisense oligonucleotides for their ability to inhibit gene expression are also disclosed.

One aspect provides antisense oligonucleotides that inhibit the expression of human replication-initiation proteins and has a sequence complementary to at least a portion of a target sequence of a human replication-initiation gene.

Another aspect is directed toward a method of preventing or treating hyperproliferative conditions by way of example but not limited to cancer, angiogenesis or neovascularization. By administering a therapeutically effective amount of an antisense oligonucleotide or by contacting the hyperproliferating cells with an effective amount of antisense oligonucleotide, expression of replication-initiation protein is inhibited.

Yet another aspect is directed toward screening and testing antisense oligonucleotides that inhibit gene expression. One embodiment involves screening an antisense oligonucleotide for inhibition of gene expression. After selecting one or more antisense oligonucleotides that inhibited gene expression, modifying those selected antisense oligonucleotides such that the oligonucleotides contain a phosphorothioate linkage between the first two nucleotides and a phosphorothioate linkage between the last two nucleotides of the sequence. The modified oligonucleotides are screened once again for inhibition of gene expression and the modified oligonucleotides that inhibited gene expression are further modified by replacing one or more internucleosidic linkages with phosphorothioate linkages.

These and other features of the claims will be appreciated from review of the following detailed description of the invention along with the accompanying figures.

DETAILED DESCRIPTION

Figure 1:
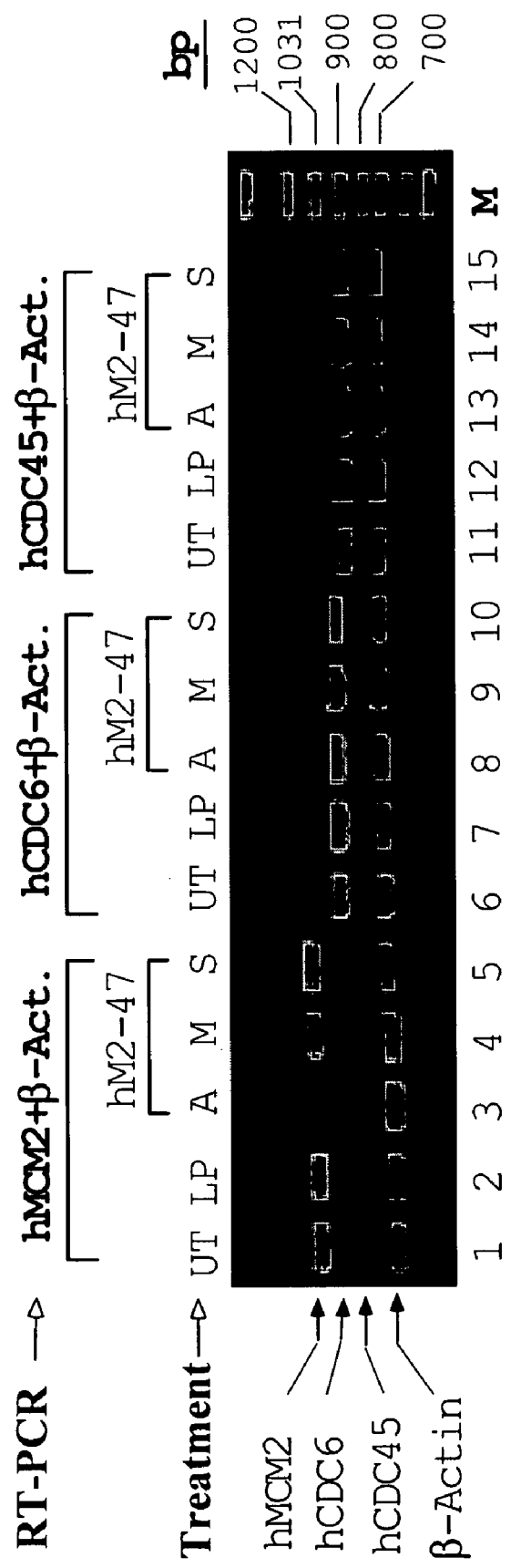
FIG. 1 illustrates the results from RT-PCR analysis of hCdc45, hCdc6, hMcm2 and the internal control β-actin gene for the cells treated with SEQ. ID. No. 16-18.

Preferred embodiments of antisense oligonucleotides that inhibit human replication-initiation protein expression as well as methods of using these antisense oligonucleotides to prevent or treat hyperproliferation conditions are described in non-limiting detail below. Methods of screening and testing active antisense oligonucleotides that inhibit gene expression are also described.

The claimed antisense oligonucleotides described by the present claims have sequences complementary to target nucleic acid sequences encoding any portion of a human replication-initiation gene. The term "antisense" refers to the complementary relationship between an antisense oligonucleotide and its complementary nucleic acid target (to which it hybridizes). An antisense oligonucleotide is formed by "targeting" an oligonucleotide to a chosen nucleic acid sequence. In this invention, the targeted sequence is any portion of an encoding sequence for a human replication-initiation protein. For example, the targeted sequence may be a sequence encoding any portion of human hCdc6 (SEQ ID No. 28), hCdc45 (SEQ ID No. 29), hMcm2 (SEQ ID No. 30), hMcm3, hMcm4, hMcm5, hMcm6, hMcm7, hOrc1, hOrc2, hOrc3, hOrc4, hOrc5, hOrc6 and hCdt1 proteins. However, other human replication-initiation proteins may be used. In one embodiment, the targeted sequence is SEQ ID Nos. 3, 6, 9, 12, 15, 18, 21, 24, or 27

The targeting process also includes determination of a site or sites within the nucleic acid sequence for the oligonucleotide interaction to occur such that inhibition of gene expression results. Once the target site or sites on the nucleic acid sequence have been identified, oligonucleotides are chosen that are sufficiently complementary to the target, i.e., hybridize sufficiently well and with sufficient specificity, which can be measured in ways which are routine in the art, for example, by Northern blot assay of mRNA expression, or reverse transcriptase PCR, Western blot, ELISA assay of protein expression, or immunoprecipitation assay of protein expression. However, other methods are known in the art and may be used. Effects on cell proliferation or tumor cell growth can also be measured, as taught in the examples below.

"Hybridization" refers to hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases that form two hydrogen bonds between them. The oligonucleotide is hybridized with sufficient specificity when a sufficient degree of complementarity affects stable and specific binding between the DNA or RNA target and the oligonucleotide. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA. The overall effect of interference with mRNA function is inhibition of human replication-initiation proteins. Practitioners in the art will appreciate that an oligonucleotide need not be 100% complementary to its target nucleic acid sequence to be specifically hybridizable. For example, in one embodiment, the claimed antisense oligonucleotide has a sequence that is 90% complementary to the target sequence.

The term "antisense oligonucleotide" as used herein means a nucleotide sequence that is complementary to the desired mRNA encoding any portion of human replication-initiation proteins. The antisense oligonucleotide is complementary to any portion of human replication-initiation protein mRNA that effectively acts as a target for inhibiting human replication-initiation protein expression.

Practitioners in the art understand that mRNA includes not only the information to encode a protein using the three letter genetic code, but also associated ribonucleotides which form a region known as the 5'-untranslated region, the 3'-untranslated region, the 5' cap region and intron/exon junction ribonucleotides. Thus, oligonucleotides may be formulated in accordance with this invention, which are targeted wholly or in part to these associated ribonucleotides as well as to the informational ribonucleotides. The oligonucleotides may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo.

Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the claims, "start codon" and "translation initiation codon" refer to the codon or codons that are used in vivo to initiate translation of an mRNA molecule transcribed from a gene encoding human replication-initiation protein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a suitable target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is also a suitable target region. The open reading frame (ORF) or "coding region," which is known in the art to refer to the region between the translation initiation codon and the translation termination codon, is also a region which may be targeted effectively. Other suitable target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a suitable target region.

Although some eukaryotic mRNA transcripts are directly translated, many contain one or more regions, known as "introns," which are excised from a pre-mRNA transcript to yield one or more mature MRNA. The remaining (and therefore translated) regions are known as "exons" and are spliced together to form a continuous mRNA sequence. mRNA splice sites, i.e., exon-exon or intron-exon junctions, are also suitable target regions, and are particularly useful in situations where aberrant splicing is implicated in disease, or where an overproduction of a particular mRNA splice product is implicated in disease. Aberrant fusion junctions due to rearrangements or deletions are also suitable targets. Targeting particular exons in alternatively spliced mRNAs are also suitable. Introns are also suitable target regions for antisense compounds targeted, for example, to DNA or pre-mRNA.

The term "oligonucleotide" refers to an oligomer or polymer of nucleotide or nucleoside monomers consisting of naturally occurring bases, sugars, and internucleosidic (backbone) linkages. The term also includes modified or substituted oligomers comprising non-naturally occurring monomers or portions thereof, which function similarly. Such modified or substituted oligomers may be preferred over naturally occurring forms because of the properties such as enhanced cellular uptake, or increased stability in the presence of nucleases. The term also includes chimeric oligonucleotides which contain two or more chemically distinct regions.

"Chimeric oligonucleotides" or "chimeras" refer to oligonucleotides that contain two or more chemically distinct regions, each made up of at least one nucleotide. These oligonucleotides typically contain at least one region of modified nucleotides that confer one or more beneficial properties (such as, for example, increased nuclease resistance, increased uptake into cells, increased binding affinity for the RNA target) and a region that is a substrate for RNase H cleavage. In one embodiment, a chimeric oligonucleotide comprises at least one region modified to increase target binding affinity, and, usually, a region that acts as a substrate for RNAse H. In one embodiment, at least one nucleotide is modified at the 2' position of the sugar, for example, a 2'-O-alkyl, 2'-O-alkyl-O-alkyl or 2'-fluoro-modified nucleotide. Such modifications are routinely incorporated into oligonucleotides and these oligonucleotides have been shown to have a higher target binding affinity than 2'-deoxyoligonucleotides against a given target. Increased affinity typically enhances the claimed antisense oligonucleotide inhibition of human replication-initiation protein expression.

RNase H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotides into which they are incorporated more resistant to nuclease digestion than the native oligodeoxynucleotide. Nuclease resistance may be measured by incubating oligonucleotides with cellular extracts or isolated nuclease solutions and measuring the extent of intact oligonucleotides remaining over time, usually by gel electrophoresis.

In one embodiment, the antisense oligonucleotides are ribonucleic or deoxyribonucleic acids and may contain naturally occurring or synthetic monomeric bases, including adenine, guanine, cytosine, thymine and uracil. As another example, the claimed antisense oligonucleotides may also contain modified bases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in the Concise Encyclopedia Of Polymer Science And Engineering 1990, pages 858-859, Kroschwitz, J. I., ed. John Wiley & Sons, those disclosed by Englisch et al. (Angewandte Chemie, International Edition 1991, 30, 613-722), and those disclosed by Sanghvi, Y. S., Chapter 15, Antisense Research and Applications 1993, pages 289-302, Crooke, S. T. and Lebleu, B., ed., CRC Press, and are incorporated by reference herein. Certain of these nucleobases are particularly useful for increasing the binding affinity of the claimed antisense oligomeric compounds, including 5-substituted pyrimidines, 6-azapyrimidines and N-2, N-6 and O-6 substituted purines, including 2-aminopropyladenine, 5-propynyluracil and 5-propynylcytosine. As another example, 5-methylcytosine substitutions increase nucleic acid duplex stability by 0.61.2.degree. C. Sanghvi, Y. S., Crooke, S. T. and Lebleu, B., eds., Antisense Research and Applications 1993, CRC Press, Boca Raton, pages 276-278 and are suitable base substitutions, particularly when combined with 2'-O-methoxyethyl sugar modifications. Modified bases may be prepared, for example, according to U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, and are incorporated by reference herein. However, other known base modifications may be used.

The modifications may also include attachment of other chemical groups such as methyl, ethyl, or propyl groups to the various parts of the oligonucleotides including the sugar, base or backbone components. Other suitable modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thiono-alkylphosphonates, thionoalkylphosphotriesters, and borano-phosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms may also be used. Modifications containing phosphorus-containing linkages may be prepared, for example, according to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, which teachings are incorporated herein by reference. However, other known base modifications may be used.

Other suitable modified oligonucleotide backbones that may be used do not include a phosphorus atom and have backbones that are formed, for example, by short chain alkyl or cycloalkyl internucleoside linkages, mixed heteroatom and alkyl or cycloalkyl internucleoside linkages, or one or more short chain heteroatomic or heterocyclic internucleoside linkages. These include, for example, those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. These modifications may be prepared, for example, according to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, and are incorporated by reference herein. However, other known base modifications may be used.

In other embodiments, the antisense oligonucleotide may contain phosphorothioate or heteroatom linkages or backbones, for example, $CH_2NHOCH_2$, $CH_2N(CH_3)OCH_2$ [also known as a methylene (methylimino) or MMI backbone], $CH_2ON(CH_3)CH_2$, $CH_2N(CH_3)N(CH_3)CH_2$ or $ON(CH_3)CH_2CH_2$ [wherein the native phosphodiester backbone is represented as $OPOCH_2$] of the above referenced U.S. Pat. No. 5,489,677 and the amide backbones of the above referenced U.S. Pat. No. 5,602,240. Other suitable modifications include phosphorothioate bonds linking between the four to six 3'-terminus nucleotides. The phosphorothioate bonds may link all the nucleotides. The phosphorothioate linkages may be mixed R and S enantiomers, or they may be stereoregular or substantially stereoregular in either R or S form. In another embodiment, the oligonucleotides are modified by at least two phosphorothioate linkages such that each oligonucleotide contains a phosphorothioate linkage between the first two nucleotides and between the last two nucleotides.

The claimed antisense oligonucleotide may also contain sugar mimetics. The oligonucleotides may have at least one nucleotide with a modified base and/or sugar, such as a 2'-O-substituted ribonucleotide. The term "2'-O-substituted" means substitution of the 2' position of the pentose moiety with an —O-lower alkyl group containing 1-6 saturated or unsaturated carbon atoms, or with an —O-aryl or allyl group having 2-6 carbon atoms, wherein such alkyl, aryl or allyl group may be un-substituted or may be substituted, e.g., with halo, hydroxy, trifluoromethyl, cyano, nitro, acyl, acyloxy, alkoxy, carboxyl, carbalkoxyl, or amino groups. The oligonucleotides of the invention may include four or five ribonucleotides 2'-O-alkylated at their 5' terminus and/or four or five ribonucleotides 2'-O-alylated at their 3' terminus. In other embodiments, antisense oligonucleotides may also contain modifications at one of the following at the 2' position: OH; F; O—, S—, or N-alkyl, O-alkyl-O-alkyl, O, S—, or N-alkenyl, or O—, S- or N-alkynyl, wherein the alkyl, alkenyl and alkynyl may be substituted or un-substituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_2$, $ON(CH_3)_2$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other suitable oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another suitable modification includes 2'-methoxyethoxy (2'-O—$CH_2CH_2COH_3$, also known as 2'-O-(2-methoxyethyl) or 2'-MOE) (Martin et al., Helv. Chim. Acta, 78, 486-504 (1995)) i.e., an alkoxyalkoxy group. Further preferred modifications include 2'-dimethylaminooxyethoxy, i.e., a $O(CH_2)_2ON(CH_3)_2$ group, also known as 2'-DMAOE, and 2'-dimethylaminoethoxyethoxy (2'-DMAEOE), and other modifications known in the art.

For example, other modifications include 2'-methoxy (2'-O—$CH_3$), 2'-aminopropoxy (2'-$OCH_2CH_2NH_2$) and 2'-fluoro (2'-F). Similar modifications may also be made at other positions on the oligonucleotides, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Modifications containing sugar mimetics may be prepared, for example, according to U.S. Pat. Nos. 4,981,957; 5,118,800; 5,319,080; 5,359,044; 5,393,878; 5,446,137; 5,466,786; 35 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, which teachings are incorporated herein by reference. However, other known base modifications may be used.

The claimed antisense oligonucleotide may also comprise nucleotide analogues wherein the structure of the nucleotide is fundamentally altered. For example, in peptide nucleic acid (PNA), both the sugar and the internucleoside linkage, i.e., the backbone, of the nucleotide units are replaced with novel groups. The base units are maintained for hybridization with an appropriate nucleic acid target compound. PNA has been shown to have excellent hybridization properties. In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. PNA analogues have been shown to be resistant to degradation by enzymes and to have extended lives in vivo and in vitro. PNAs also bind more strongly to a complementary DNA sequence than to a naturally occurring nucleic acid molecule due to the lack of charge repulsion between the PNA strand and the DNA strand. PNA compounds may be prepared, for example, according to U.S. Pat. Nos. 5,539,082; 5,714,331; and 5,719,262. Further teaching of PNA compounds can be found in Nielsen et al., Science, 254, 1497-1500 (1991), and is incorporated by reference herein.

Other embodiments may also include other nucleotides comprising polymer backbones, cyclic backbones, or acyclic backbones. For example, suitable nucleotides may comprise morpholino backbone structures (U.S. Pat. No. 5,034,506 (33)) or other modified linkages.

In other embodiments, the antisense oligonucleotides are "nuclease resistant" when they have either been modified such that they are not susceptible to degradation by DNA and RNA nucleases or alternatively they have been placed in a delivery vehicle that in itself protects the oligonucleotides from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example liposomes.

The claimed antisense oligonucleotides may also contain groups for improving the pharmacokinetic properties of oligonucleotides. For example, oligonucleotides may be linked to one or more moieties or conjugates which enhance the activity, cellular distribution or cellular uptake of the oligonucleotides. Such moieties include but are not limited to lipid moieties such as a cholesterol moiety (Letsinger et al., Proc. Natl. Acad. Sci. USA, 86, 6553-6556 (1989)), cholic acid (Manoharan et al., Bioorg. Med. Chem. Lett., 4, 1053-1059 (1994)), a thioether, e.g., hexyl-S-tritylthiol (Manoharan et al., Ann. N.Y. Acad. Sci., 660, 306-309 (1992); Manoharan et al., Bioorg. Med. Chem. Let., 3, 2765-2770 (1993)), a thiocholesterol (Oberhauser et al., Nucl. Acids Res., 20, 533-538 (1992)), an aliphatic chain, e.g., dodecandiol or undecyl residues (Saison-Behmoaras et al., EMBO J., 10, 1111-1118 (1991); Kabanov et al., FEBS Lett., 259, 327-330 (1990); Svinarchuk et al., Biochimie, 75, 49-54 (1993)), a phospholipid, e.g., di-hexadecyl-rac-glycerol or triethylammonium 1,2-di-O-hexadecyl-rac-glycero-3-H-phosphonate (Manoharan et al., Tetrahedron Lett., 36, 3651-3654 (1995); Shea et al., Nucl. Acids Res., 18, 3777-3783 (1990)), a polyamine or a polyethylene glycol chain (Manoharan et al., Nucleosides & Nucleotides, 14, 969-973 (1995)), or adamantane acetic acid (Manoharan et al., Tetrahedron Lett., 36, 3651-3654 (1995)), a palmityl moiety (Mishra et al., Biochim. Biophys. Acta, 1264, 229-237 (1995)), or an octadecylamine or hexylaminocarbonyl-oxycholesterol moiety (Crooke et al., J. Pharmacol. Exp. Ther., 277, 923-937 (1996)). However, other pharmacokinetic-enhancing moieties known in the art are also suitable. For example, many of these conjugates may be prepared according to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, and are incorporated by reference herein. However, other known pharmacokinetic-enhancing modifications may be used.

In other embodiments, antisense oligonucleotides include mutations, such as substitutions, insertions and deletions. Preferably, there will be less that 10% of the sequence having mutations. In one embodiment, the antisense oligonucleotide sequence is at least 90% complementary to the target sequence.

It is not necessary for all positions in a given compound to be uniformly modified, and in fact, more than one of the aforementioned modifications may be incorporated in a single compound or even at a single nucleoside within an oligonucleotide.

The claimed antisense oligonucleotides may be formed by solid phase synthesis or any other means known in the art. Equipment for such synthesis is sold by several vendors including APPLIED BIOSYSTEMS®. Similar techniques to prepare modified oligonucleotides such as phosphorothioates and alkylated derivatives are also known, as are techniques and commercially available modified amidites and controlled-pore glass (CPG) products such as biotin, fluorescein, acridine or psoralen-modified amidites and/or CPG (available from GLEN RESEARCH®, Sterling Va.) to synthesize fluorescently labeled, biotinylated or other modified oligonucleotides such as cholesterol-modified oligonucleotides.

In one embodiment, antisense oligonucleotides are selected from the sequence complementary to the human replication-initiation gene such that the sequence exhibits little likelihood of showing duplex formation, hair-pin formation, and homooligomer/sequence repeats, but has an increased potential to bind to the replication-initiation gene sequences. These properties may be determined using a suitable computer modeling program such as MFOLD™. Zuker, M., In "RNA Biochemistry and Biotechnology", J. Barciszewski & B. F. C. Clark, eds., NATO ASI Series, Kluwer Academic Publishers, incorporated by reference herein.

In one embodiment, antisense oligonucleotides generally comprise from at least about 3 nucleotides or nucleotide analogs, more preferably they are at least about 5 nucleotides, more preferably they are at least about 7 nucleotides, more preferably they are at least about 9 nucleotides, and most preferably they are at least about 16 nucleotides. The antisense oligonucleotides are preferably less than about 100 nucleotides or nucleotide analogs, more preferably, less than about 50 nucleotides or nucleotide analogs, most preferably less than about 35 nucleotide or nucleotide analogs. In one embodiment, the antisense oligonucleotide has the sequence identified in SEQ. ID. Nos. 1, 4, 7, 10, 13, 16, 19, 22, or 25. In another embodiment, the sequence contains an 8 nucleotide base portion selected from SEQ. ID. Nos. 1, 4, 7, 10, 13, 16, 19 22, and 25.

Other embodiments of antisense oligonucleotides include bioequivalent compounds, for example, pharmaceutically acceptable salts and prodrugs, such as salts, esters, or salts of such esters, or any other compound which, upon administration to an animal including a human, is capable of providing (directly or indirectly) the biologically active metabolite or residue thereof. For example, embodiments include acceptable salts of the nucleic acids of oligonucleotides and prodrugs of such nucleic acids. Pharmaceutically acceptable salts are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," J. of Pharma Sci., 66, 1-19 (1977)), incorporated by reference herein.

Suitable pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

In another embodiment, the antisense oligonucleotide may additionally or alternatively be prepared to be delivered as an pro-drug. The term pro-drug refers to therapeutic agents that are prepared in inactive form and converted to active form (i.e., drug) within the body or cells thereof by the action of endogenous enzymes or other chemicals and/or conditions. In one embodiment, pro-drug versions of the claimed oligonucleotides are prepared as SATE [(S-acetyl-2-thioethyl) phosphate] derivatives according to the methods disclosed in WO 93/24510 to Gosselin et al., published Dec. 9, 1993, incorporated by reference herein.

In another aspect, methods for inhibiting human replication-initiation protein expression and for interfering with cell hyperproliferation were developed using antisense oligonucleotides targeted to portions of human replication-initiation mRNA. In one embodiment, a method of treating or preventing a hyperproliferative condition comprises administering to a human or cells thereof a therapeutically effective amount of antisense oligonucleotides having a sequence complementary to a target sequence encoding mRNA of a human replication-initiation gene, wherein expression of the replication-initiation protein is inhibited. In another embodiment, the hyperproliferating cells are contacted with a therapeutically effective amount of claimed antisense oligonucleotides. In another embodiment, tissues or cells are contacted with oligonucleotides. To "contact" tissues or cells with an oligonucleotides or oligonucleotides means to add the oligonucleotides, for example, in a liquid carrier, to a cell suspension or tissue sample, either in vitro or ex vivo, or to administer the oligonucleotides to cells or tissues within an animal. However, other contact means known in the art may be used. It will be appreciated by those skilled in the art that equivalent methods or agents that inhibit the expression and/or activities of replication-initiation proteins are contemplated, for example, RNAi, and including compounds such siRNA or the like in RNA Interference for inhibition of gene expression as described in Harboth et al., "Identification of essential genes in cultured mammalian cells using small interfering RNAs" Journal of Cell Science 114, 4557-4565 (2001), which teachings are incorporated herein by reference.

In one embodiment, the hyperproliferative condition is cancer, angiogenesis, neovascularization, psoriasis, blood vessel restenosis, or atherosclerosis or similar condition. In another embodiment, the targeted sequence encodes a portion of hCdc6, hCdc45, hMcm2, hMcm3, hMcm4, hMcm5, hMcm6, hMcm7, hOrc1, hOrc2, hOrc3, hOrc4, hOrc5, hOrc6 or hCdt1 genes.

claimed antisense oligonucleotide compounds may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotides. Such compositions and formulations readily known in the art and easily incorporated with embodiment of the present claims.

Pharmaceutical compositions comprising the claimed antisense oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems, 8, 91-192 (1991); Muranishi, Critical Reviews in Therapeutic Drug Carrier Systems, 7, 1-33 (1990)), incorporated by reference herein. One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., Critical Reviews in Therapeutic Drug Carrier Systems, p. 92 (1991); Muranishi, Critical Reviews in Therapeutic Drug Carrier Systems, 7, 1 (1990); El-Hariri et al., J. Pharm. Pharmacol., 44, 651-654 (1992)), incorporated by reference herein. Complex formulations comprising one or more penetration enhancers may be used. For example, bile salts may be used in combination with fatty acids to make complex formulations.

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934-935), incorporated by reference herein. Various natural bile salts, and their synthetic derivatives, act as penetration enhancers.

Thus, the term "bile salt" includes any of the naturally occurring components of bile as well as any of their synthetic derivatives.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, p. 92 (1991); Muranishi, Critical Reviews in Therapeutic Drug Carrier Systems, 7, 1-33 (1990); Buur et al., J. Control Rel., 14, 43-51 (1990)), incorporated by reference herein. Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems, p. 92 (1991)); and perfluorochemical emulsions, such as FC-43 (Takahashi et al., J. Pharm. Phamacol., 40, 252-257 (1988)), incorporated by reference herein.

Non-surfactants include, for example, unsaturated cyclic ureas, 1-alkyl- and 1-alkenylazacyclo-alkanone derivatives (Lee et al., Critical Reviews in Therapeutic Drug Carrier Systems, p. 92 (1991)), incorporated by reference herein; and non-steroidal anti-inflammatory agents such as diclofenac sodium, indomethacin and phenylbutazone (Yamashita et al., J. Pharm. Pharmacol., 39, 621-626 (1987)), and incorporated by reference herein.

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co administration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor.

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404, incorporated by reference herein. However, other pharmaceutically acceptable carriers known in the art may be used.

The claimed compositions of the present invention may additionally contain other adjunct components conventionally found in pharmaceutical compositions at their art-established usage levels. For example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the claimed compositions.

The formulation of claimed compositions and their subsequent administration is believed to be within the skill in the art. In general, for therapeutics, a patient suspected of needing such therapy is given one or more oligonucleotides in accordance with the invention, commonly in a pharmaceutically acceptable carrier, in amounts and for periods which will vary depending upon the nature of the particular disease, its severity and the patient's overall condition.

Suitable pharmaceutical compositions may be administered in a number of ways depending upon whether local or systemic treatment is desired and upon the area to be treated. Administration may be topical (including but not limited to ophthalmic, vaginal, rectal, intranasal, epidermal, and transdermal), oral or parenteral. Parenteral administration may include, for example, intravenous drip, intravenous injection, subcutaneous, intraperitoneal, intraocular, intravitreal or intramuscular injection, pulmonary administration, e.g., by inhalation or insufflation, or intracranial, e.g., intrathecal or intraventricular, administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. However, other formulations known in the art may also be used.

Compositions for oral administration include, for example, powders or granules, suspensions or solutions in water or non-aqueous media, capsules, sachets, or tablets. Thickeners, flavorings, diluents, emulsifiers, dispersing aids or binders may be desirable. Practitioners in the art understand that other oral compositions known in the art may also be used.

Compositions for parenteral administration may include sterile aqueous solutions that may also contain buffers, diluents and other suitable additives. In some cases it may be more effective to treat a patient with claimed oligonucleotides in conjunction with other traditional therapeutic modalities in order to increase the efficacy of a treatment regimen. The term "treatment regimen" refers to therapeutic, palliative and prophylactic modalities. For example, a patient may be treated with conventional chemotherapeutic agents, particularly those used for tumor and cancer treatment. In another embodiment, the claimed composition comprises a chemotherapeutic agent and a claimed antisense oligonucleotide that inhibits expression of human replication-initiation protein in cells. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide, trimetrexate, teniposide, carboplatin, topotecan, irinotecan, gemcitabine, cisplatin and diethylstilbestrol (DES). See, generally, The Merck Manual of Diagnosis and Therapy, 15th Ed. 1987, pp. 1206-1228, Berkow et al., eds., Rahway, N.J., incorporated by reference herein. Obviously, other chemotherapeutic agents known in the art may be used. When used with a claimed antisense oligonucleotide, such chemotherapeutic agents may be used individually (e.g., 5-FU and one or more oligonucleotides), sequentially (e.g., 5-FU and one or more oligonucleotides for a period of time followed by MTX and one or more oligonucleotides), or in combination with one or more other such chemotherapeutic agents (e.g., 5-FU, MTX and one or more oligonucleotides, or 5-FU, radiotherapy and one or more oligonucleotides).

Other drugs such as leucovorin, which is a form of folic acid used as a "rescue" after high doses of methotrexate or other folic acid agonists, may also be administered. In some embodiments, 5-FU and leucovorin are given in combination as an IV bolus with the compounds of the invention being provided as an IV infusion.

In addition to such pharmaceutical carriers, cationic lipids may be included in the formulation to facilitate oligonucleotide uptake. One such composition shown to facilitate uptake is Lipofectin (BRL, Bethesda Md.).

Regardless of the method by which the claimed antisense oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech., 6, 698-708 (1995)), incorporated by reference herein.

Dosing of the claimed antisense oligonucleotides is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be calculated using in vitro and in vivo animal EC50 studies. For example, given the molecular weight of compound (derived from oligonucleotide sequence and chemical structure) and an effective dose such as an IC50, for example (derived experimentally), a dose in mg/kg is routinely calculated.

One embodiment diagnoses abnormal proliferative states in tissue or other samples from patients, for example, suspected of having a hyperproliferative disease such as cancer, angiogenesis, neovascularization, psoriasis, blood vessel restenosis, or atherosclerosis. However, other abnormal proliferative conditions are contemplated within the scope of the claims. For example, in one embodiment, an effective amount of a claimed antisense oligonucleotide is administered to or contacted with human cells wherein the antisense oligonucleotide has a sequence complementary to a target sequence encoding mRNA of a human replication-initiation gene, wherein expression of the replication-initiation protein is inhibited. An effective amount of claimed oligonucleotide is readily determined by the skilled practitioner.

A number of assays may be formulated employing the claimed antisense oligonucleotides. For example, one assay comprises contacting a tissue sample with one or more oligonucleotides of the invention under conditions selected to permit detection and, usually, quantitation of such inhibition. In another embodiment, an assay using the claimed antisense oligonucleotides distinguishes tumors associated with human replication-initiation proteins from tumors having other etiologies, in order that an efficacious treatment regime can be designed.

In other embodiments, the claimed methods and antisense oligonucleotides are used in diagnostics, therapeutics, prophylaxis, and as research reagents and in kits. Since the claimed antisense oligonucleotides hybridize to nucleic acids encoding a human replication-initiation protein, sandwich, colorimetric and other assays are easily be constructed to exploit this fact. Detection and quantitation of oligonucleotides are skills readily known in the art. For example, enzyme conjugation, radiolabelling or any other suitable detection systems may be used to detect hybridization of the claimed oligonucleotides. Kits for detecting the presence or absence of human replication-initiation protein mRNA may also be prepared.

The claimed methods and antisense oligonucleotides may also be used for research purposes. Thus, the specific hybridization exhibited by the oligonucleotides may be used for assays, purifications, cellular product preparations and in other methodologies which may be appreciated by persons of ordinary skill in the art.

The claimed antisense oligonucleotides are also useful for detection and diagnosis of human replication-initiation protein expression. For example, radiolabeled oligonucleotides can be prepared by $^{32}$P labeling at the 5' end with polynucleotide kinase (Sambrook et al., Molecular Cloning. A Laboratory Manual, Cold Spring Harbor Laboratory Press, 1989, Volume 2, p. 10.59), incorporated by reference herein. Radiolabeled oligonucleotides are then contacted with tissue or cell samples suspected of human replication initiation protein expression and the sample is washed to remove unbound oligonucleotides. Radioactivity remaining in the sample indicates bound oligonucleotides (which in turn indicates the presence of human replication-initiation protein) and can be quantitated, for example, using a scintillation counter or other means readily known in the art. Radiolabeled oligonucleotides can also be used to perform autoradiography of tissues to determine the localization, distribution and quantitation of human replication initiation protein expression for research, diagnostic or therapeutic purposes. In these embodiments, tissue sections are treated with radiolabeled oligonucleotides and washed as described above, then exposed to photographic emulsion according to routine autoradiography procedures. The emulsion, when developed, yields an image of silver grains over the regions expressing human replication-initiation protein. Quantitation of the silver grains permits protein expression to be detected.

Analogous assays for fluorescent detection of human replication-initiation expression employ claimed antisense oligonucleotides that are conjugated with fluorescein or other fluorescent tags instead of radiolabelling. Such conjugations are routinely accomplished during solid phase synthesis using fluorescently labeled amidites or CPG (e.g., fluorescein-labeled amidites and CPG available from GLEN RESEARCH®, Sterling Va. See 1993 Catalog of Products for DNA Research, Glen Research, Sterling Va., p. 21), incorporated by reference herein.

Each of these assay formats is known in the art and is readily adapted as methods for detection of human replication-initiation protein expression in accordance with the claims as a novel and useful means to detect human replication-initiation protein expression.

Another aspect provides a method of identifying antisense oligonucleotides that inhibit expression of a gene. In one embodiment, the method involves screening an antisense oligonucleotide for inhibition of gene expression, wherein the oligonucleotide contains a phosphodiester DNA backbone. After selecting one or more antisense oligonucleotides that inhibit gene expression, at least two internucleosidic linkages of the selected antisense oligonucleotides are modified such that the oligonucleotides contain a phosphorothioate linkage between the first two nucleotides and between the last two nucleotides of the sequence. Screening the modified oligonucleotides for inhibition of gene expression results in selection of one or more antisense oligonucleotides that may inhibit gene expression as well as have partially modified backbones. Once active antisense oligonucleotides have been selected, one or more oligonucleotides linkages is replaced with more phosphorothioate linkages.

For example, in one embodiment, antisense oligonucleotides were designed, screened and tested according to the present claims. Extensive base pairing exists in the secondary structure of mRNAs, therefore, in one embodiment only the single-stranded regions of mRNAs are used as targets for antisense oligonucleotides. With the known sequences of the cDNA of the replication-initiation proteins in human (Williams, U.S. Pat. No. 5,851,821; Saha, P. et al., J. Biol. Chem., 50, 6075-6086 (1990); Todorov, I. T, et al., J. Cell Sci., 107, 253-265 (1994)), incorporated by reference herein, computer modeling, for example MFOLD™ (Zuker, M., In "RNA Biochemistry and Biotechnology", J. Barciszewski & B. F. C. Clark, eds., NATO ASI Series, Kluwer Academic Publishers.) was used to predict the secondary structures of mRNAs, and then antisense oligonucleotides were targeted to the putative single-stranded areas along the entire length of the mRNAs. One hundred and seventy antisense oligonucleotides with normal phosphodiester DNA backbones targeted to the hCdc6, hMcm2 and hCdc45 genes were designed and subjected to initial screening for their activities to inhibit cancer cell growth in tissue culture. Of the 170 oligonucleotides, 66 were targeted to hCdc6 (named hC6-1 through hC6-66), 64 to hMcm2 (hM2-1 through hM2-64), and 40 to hCdc45 (hC45-1 through hC45-40). All 170 oligonucleotides and the modified oligonucleotides containing phosphorothioate linkages described below were custom-synthesized and purified to ~99% (HPSF™—"Highly Purified Salt Free"—grade; MGW BIOTECH™), and were further ethanol-precipitated twice to remove small-molecule impurities.

The human cancer cell lines initially used were a liver cancer cell line (called the Chang's Liver Cancer Cells) and HeLa cells. Other human cancer (such as HoNe1, T-Tn, HepG2 and Hep3B) and normal (L-02) cell lines were also used to test the activities and specificity of the oligonucleotides. Cells (5000/well) were seeded in 96-well plates and grown in 100 µl/well of the DMEM medium (Life Technologies) containing fetal bovine serum (10%), penicillin and streptomycin. Cells were incubated at 37.degree. C. with 5% $CO_2$. One day later, the medium was changed to the same medium (50 µl) but without serum, and the oligonucleotides (1 µM) were added to the cell culture as conjugates with the cationic liposome carrier Lipofectin (1.7%) or LipofectAMiNE Plus (2.4%) (Life Technologies) in a total transfection volume of 70 µl. A mixture of all 170 oligonucleotides (1 µM total) conjugated with the carrier, the carrier without oligo, and individual oligonucleotides without the carrier were used as the negative controls. Three hours later, the medium was changed back to the regular medium containing serum. Two days later, the number of viable cells was determined by the tetrazolium assay using WST-1 as described (Ishiyama et al., 1996). The WTS-1 assay is more sensitive and accurate and has a wider dynamic range than the MTT assay. It was found that 16 of the 170 oligonucleotides tested could inhibit cancer cell growth and kill cancer cells, resulting in the number of viable cells being 20-40% compared to the untreated cells. Oligonucleotides without the carrier had no activity (90-100% of cells survived), while the carrier without oligo or the mixture of all 170 oligonucleotides conjugated with the carrier gave 60-70% live cells compared to the untreated cells. These results indicated that while the carrier was necessary, it was somewhat cytotoxic when used in much a high concentration that was needed to carry the large amount of oligonucleotides with phosphodiester DNA backbones into the cells. (The toxicity of the carrier was reduced by lowering the concentrations of the carriers for the modified oligonucleotides in later experiments; below.)

The 16 antisense oligonucleotides that were tested active in the initial screening were then subjected to further testing for their activities towards the cancer cells. To increase resistance to exonucleases which are present in the growth medium containing serum, both the 5'- and 3'- ends of the oligonucleotides were modified by phosphorothioate (PT) linkages, such that each oligo contains a PT linkage between the first two nucleotides and between the last two nucleotides. The sense and mismatched oligonucleotides that were PT-modified in the same way were used as the negative controls. Note that the sense oligonucleotides are complementary to the corresponding antisense oligonucleotides and that 3 to 4 of the nucleotides in each antisense oligo were exchanged to generate the mismatched oligo, keeping base composition unchanged (Table 1).

While the cells were grown in the same way as described above, the end-modified oligonucleotides (0.7 µM) were transfected into the cells as conjugates with LipofectAMINE Plus (2%) or LipofectAMINE-2000 (0.7%) in 70 µl or 100 µl, respectively, of the OPTI-MEM™ medium (Life Technologies) without serum as the transfection medium. Three (for LipofectAMINE Plus) or four (for LipofectAMINE-2000) hours later, the medium was changed back to the regular growth medium containing serum. During screening of these modified oligonucleotides, the number of viable cells was determined by the WST-1 assay two days post-transfection. Nine of these end-modified oligonucleotides showed strong activities to not only prevent cancer cell growth, but also to induce cancer cell death in culture. Two days after a single treatment, the number of live cancer cells was ranged from 6.7% (with hC45-18a) to 18.9% (with hC45-30a) compared to the untreated cells (Table 1). Moreover, actual cell death and cell lysis were evident as observed under a light microscope and demonstrated by a series of cell death assays, for example, measuring DNA fragmentation on the activity of LDH dehydrogenase released into the medium upon cell death. One or both of the negative control oligonucleotides for five of the nine active antisense oligonucleotides (hC6-35, hM2-47, hC45-18, hC45-27 and hC45-30) were not nearly as active as the antisense oligonucleotides, indicating good specificity of these four antisense oligonucleotides towards the targeted genes. However, the sense and mismatched control oligonucleotides for the other four active antisense oligonucleotides (hC6-39, hC6-60, hM2-13 and hM2-34) were also quite active. The activities of the control oligonucleotides were likely due to unintended inhibition of other unknown genes or cell functions by these control oligonucleotides, which does not necessarily mean that the antisense oligonucleotides were non-specific in their anti-cancer cell activities.

TABLE 1

Summary of the Nine End-Modified Antisense Oligonucleotides with Anti-Cancer Cell Activities

| Oligo Name[a] | Length (nt) | SEQ ID No. | Sequence (5'→3') | % Viable Cells |
|---|---|---|---|---|
| hC6-35a | 16 | 1 | AAG GTG GGA AGT TCA A | 13.5 |
| hC6-35m | 16 | 2 | AAG aTG GGt AGg TCA A | 31.5 |
| hC6-35s | 16 | 3 | TTG AAC TTC CCA CCT T | 28.1 |
| hC6-39a | 18 | 4 | CTC CCT CTT GGC TCA AGG | 15.3 |
| hC6-39m | 18 | 5 | CTC CCa CCT GGt TCt AGG | 7.3 |
| hC6-39s | 18 | 6 | CCT TGA GCC AAG AGG GAG | 21.8 |
| hC6-60a | 19 | 7 | AGC CTG GCC AAC ATG GTA A | 9.1 |
| hC6-60m | 19 | 8 | AGC CgG aCC AgC ATt GTA A | 18.1 |
| hC6-60s | 19 | 9 | TTA CCA TGT TGG CCA GGC T | 16.1 |
| hM2-13a | 16 | 10 | CTT GAA GAC GTT GTG G | 13.7 |
| hM2-13m | 16 | 11 | CTT tAA GgC GTa GTG G | 19.4 |
| hM2-13s | 16 | 12 | CCA CAA CGT CTT CAA G | 21.1 |
| hM2-34a | 16 | 13 | CAG AAC CAG GGC CCC A | 9.9 |
| hM2-34m | 16 | 14 | CAG cAg CAG GcC aCC A | 11.1 |
| hM2-34s | 16 | 15 | TGG GGC CCT GGT TCT G | 9.9 |
| hM2-47a | 17 | 16 | TCC CGC AGA TGG ATG CG | 18.9 |
| hM2-47m | 17 | 17 | TCC CtC AGg TGG AaG CG | 63.3 |
| hM2-47s | 17 | 18 | CGC ATC CAT CTG CGG GA | 34.1 |
| hC45-18a | 20 | 19 | AGG CTG TCA TGG AGG GAC CA | 6.7 |
| hC45-18m | 20 | 20 | AGG CTc TgA gGG AGt GAC CA | 9.5 |
| hC45-18s | 20 | 21 | TGG TCC CTC CAT GAC AGC CT | 39.1 |
| hC45-27a | 19 | 22 | CGC GCA TGT CCT TCA TCC C | 11.8 |
| hC45-27m | 19 | 23 | CGC GtA TGc CCa TCt TCC C | 30.7 |
| hC45-27s | 19 | 24 | GGG ATG AAG GAC ATG CGC G | 12.1 |
| hC45-30a | 16 | 25 | GAA GTG ATC TGT CCC T | 18.4 |
| hC45-30m | 16 | 26 | GAg GTG AaC TtT CCC T | 50.1 |
| hC45-30s | 16 | 27 | AGG GAC AGA TCA CTT C | 55.6 |

Notes:
[a]The oligonucleotides names start with the gene name (hC6: hCdc6; hM2: hMcm2; hC45: hCdc45), followed by a hyphen, the antisense oligo number as appeared in the initial screening, and the letter "a", "m" or "s" depending on whether the oligonucleotides are antisense, mismatched or sense, respectively. All mismatched oligonucleotides except hM2-34m have the same base composition as the corresponding antisense oligonucleotides.
[c]All oligonucleotides in this table contain a phosphorothioate (PT) linkage between the first two nucleotides and between the last two nucleotides. Lower case letters designate altered bases in the mismatched oligonucleotides compared to the antisense oligonucleotides.
[d]% Viable Cells is the ratio of the WST-1 assay reading for the treated cells over that for the untreated cells. The liposome carrier without oligo gave 75-85% viable cells compared to the untreated cells. The antisense oligonucleotides that were active towards cancer cells were not active towards the normal MCF-10 cells (~80% viable, similar to carrier without oligo).

The nine active antisense oligonucleotides were checked to see if they actually inhibited the expression of the targeted genes. Total RNA was extracted using the TRIzol® kit (LIFE TECHNOLOGIES®) according to the manufacturer's instruction, and proteins were extracted using a commonly used lysis buffer (50 mM HEPES, pH 7.6, 150 mM NaCl, 1 mM EGTA, 1.5 mM $MgCl_2$, 10% glycerol, 2 mM DTT, 1% Triton X-100, plus protease and phosphatase inhibitors). The mRNA levels were examined by RT-PCR using specific primers to the targeted and control genes and the proteins by Western blotting using specific antibodies to the proteins encoding by the targeted genes. It was found that the antisense oligonucleotides that were active in preventing cancer cell growth and killing cancer cells reduced the levels of both the mRNAs and proteins of the targeted genes by 70-90% compared to the untreated cells and those treated with control oligonucleotides or carrier alone (see Examples below).

Four of the active and relatively specific antisense oligonucleotides (hC6-35a, hM2-47a, hC45-18a, and hC45-30a) were chosen for further characterization with the oligonucleotides fully modified with phosphorothioate (PT) linkages (resistant to both exo- and endo-nuclease digestion). The four fully PT-modified antisense oligonucleotides were active in much lower concentrations (at 0.1-0.2 µM) than the phosphodiester (1 µM) or end-modified oligonucleotides (0.7 µM) with the same DNA sequences.

To assist in understanding the present invention, the following examples are included and describe the results of a series of experiments. The following examples relating to this invention should not be construed to specifically limit the invention or such variations of the invention, now known or later developed, which fall within the scope of the invention as described and claimed herein.

EXAMPLES

Example 1

Initial Screening of the 170 Antisense Oligonucleotides with Phosphodiester DNA Backbones. The Chang's Liver Cancer Cells and HeLa cells were used to test the activities and specificity of the oligonucleotides. Cells (5000/well) were seeded in 96-well plates and grown in 100 µl/well of DMEM medium containing fetal bovine serum (10%), penicillin and streptomycin. One day later, the medium was changed to the same medium (50 µl) but without serum, and the oligonucleotides (1 µM) were added to the cell cultures as conjugates with Lipofectin (1.7%) or LIPOFECTAMINE PLUS™ (2.4%) (The total transfection volume was 70 µl). A mixture of all 170 oligonucleotides (1 µM total) conjugated with the carrier, the carrier without oligo, and individual oligonucleotides without the carrier were used as the negative controls. Three hours later, the medium was changed back to the regular medium containing serum. Two days later, the number of viable cells was determined by the WST-1 assay. Among the 170 oligonucleotides tested, 16 of them could inhibit cell growth and kill cancer cells; 20-40% of cells remained viable compared to the untreated cells. Oligonucleotides without the carrier had no activity (90-100% of cells survived), while the carrier without oligo or the mixture of all oligonucleotides conjugated with the carrier resulted in 60-70% live cells compared to the untreated cells. The carrier was somewhat cytotoxic when used in much a high concentration that was needed for carrying the large amounts of oligonucleotides with phosphodiester DNA backbones into the cells. (The toxicity of the carrier was minimized by lowering the concentrations of the carriers used for the modified oligonucleotides in later experiments; below.)

Example 2

Further Testing of the 16 Oligonucleotides That Showed Anti-Cancer Cell Activities in the Initial Screening. The 16 antisense oligonucleotides and their corresponding mismatched and sense control oligonucleotides were produced with their 5'- and 3'-end modified with phosphorothioate linkages, and tested for their activities towards cancer cells. The oligonucleotides (0.7 µM) were transfected into the Chang's Liver Cancer Cells or HeLa cells as conjugates with LIPO-FECTAMINE PLUS™ (2%) or LIPOFECTAMINE-2000™ (0.7%) in 70 µl or 100 µl, respectively, of the OPTI-MEM™ medium without serum as the transfection medium. The number of viable cells was measured as described in Example 1 and cell death was measured by the LDH dehydrogenase release assay. Nine of these 16 oligonucleotides showed strong anti-cancer cell activities (Table 1). The number of viable cancer cells in the oligo-treated culture was ranged from 6.7% (for hC45-18a) to 18.9% (for hC45-30a) compared to the untreated cells. One or both of the negative control oligonucleotides for five antisense oligonucleotides (hC6-35, hM2-47, hC45-18, hC45-27 and hC45-30) were not nearly as active as the antisense oligonucleotides. However, the sense and mismatched control oligonucleotides for the other four antisense oligonucleotides (hC6-39, hC6-60, hM2-13 and hM2-34) were also quite active, perhaps due to unintended inhibition of other unknown genes or cell functions by these control oligonucleotides.

Example 3

The Antisense Oligonucleotides hM2-47a with Anti-Cancer Cell Activities Inhibited the Expression of the Target Gene hMcm2, But Not of hCdc6 or hCdc45. The Chang's Liver Cancer Cells were treated with the antisense oligonucleotides hM247a (0.7 µM) or the corresponding mismatched (hM2-47m) or sense (hM2-47s) control oligonucleotides (see Table 1) conjugated with LIPOFECTAMINE-2000™ (0.7%) in 100 µl of the OPTI-MEM™ medium without serum for 4 hrs. The cells were then grown in regular DMEM containing serum for 1.5 hrs before RT-PCR analysis was carried out with total RNA isolated from the treated and untreated cells using the TRIZOL® Reagent (LIFE TECHNOLOGIES®). RNA was reverse-transcribed into first strand cDNA using a cDNA synthesis kit (MBI FERMENTAS®) with oligo(dT) as the primer. The same cDNA sample was then used as the template for PCR amplification of a specific fragment of hMcm2, hCdc6, and hCdc45, respectively, while a fragment of the internal control β-actin gene was co-amplified with each of the three initiation genes (FIG. 1). The antisense oligonucleotides hM2-47a specifically reduced the mRNA level of the target gene hMcm2 (Lane 3), but not the other replication-initiation gene hCdc6 (Lanes 8) or hCdc45 (Lane 13). UT: untreated cells; LP: liposome without oligonucleotides; A: antisense oligonucleotides; M: mismatched oligonucleotides.

Example 4

Figure 2:
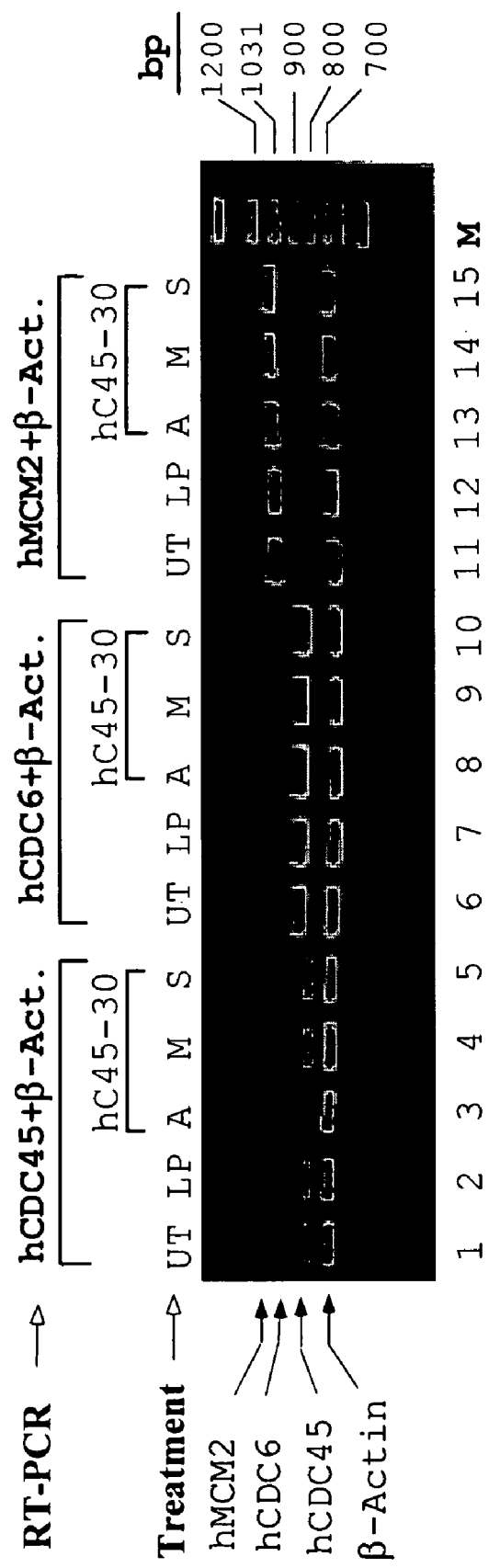
FIG. 2 illustrates the results from RT-PCR analysis of hCdc45, hCdc6, hMcm2 and the internal control β-actin gene for the cells treated with the SEQ. ID. Nos. 25-27.

The Antisense Oligonucleotides hC45-30a with Anti-Cancer Cell Activities Inhibited the Expression of the Target Gene hCdc45. But Not of hMcm2 or hCdc6. The Chang's Liver Cancer Cells were treated with the antisense (A) oligonucleotides hC45-30a (0.7 µM) or the corresponding mismatched (M) or sense (S) control oligonucleotides (see Table 1) in the same way as described in Example 3. The levels of the mRNA of hCdc45, hCdc6, hMcm2, and the β-actin gene, respectively, were measured by RC-PCR analysis (FIG. 2) as described in Example 3. The antisense oligonucleotides hC45-30a specifically diminished the mRNA level of the target gene hCdc45 (Lane 3), but not the other replication-initiation gene hCdc6 (Lanes 8) or hMcm2 (Lane 13). UT: untreated cells; LP: liposome without oligonucleotides.

Example 5

Figure 3:
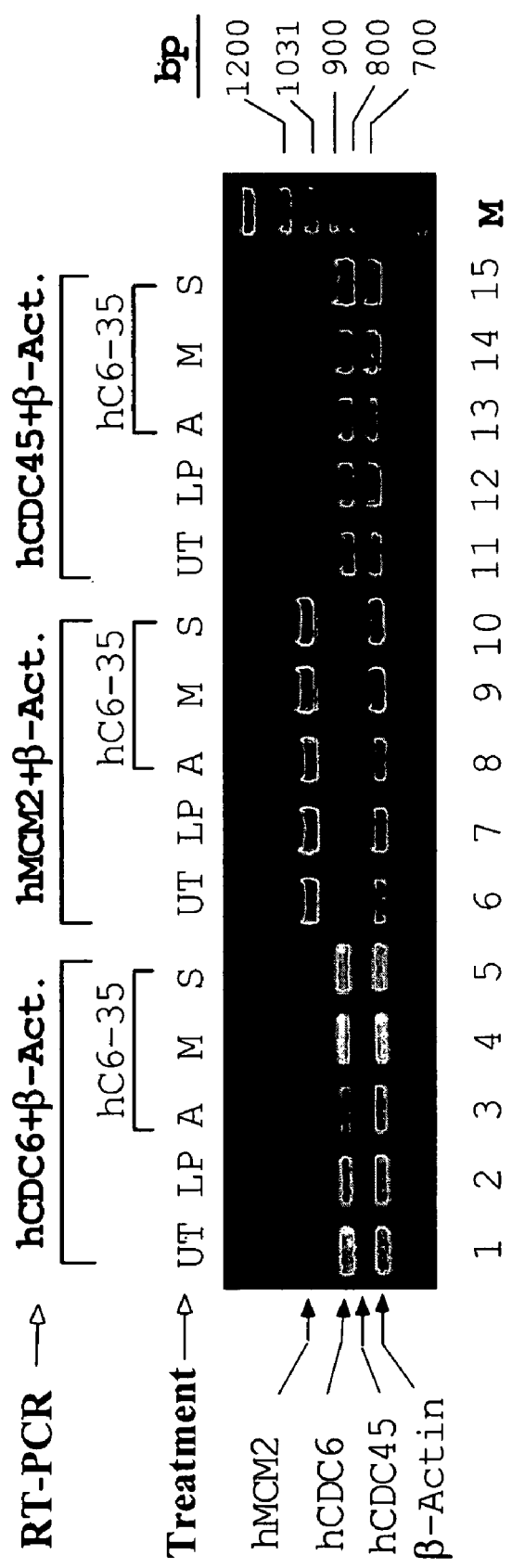
FIG. 3 illustrates the results from RT-PCR analysis of hCdc45, hCdc6, hMcm2 and the internal control β-actin gene for the cells treated with the antisense oligonucleotide SEQ. ID. No. 1 or the control oligonucleotides.

The Antisense Oligonucleotides hC6-35a with Anti-Cancer Cell Activities Reduced the Expression of the Target Gene hCdc6. But Not of hMcm2 or hCdc45. The Chang's Liver Cancer Cells were treated with the antisense (A) oligonucleotides hC6-35a (0.7 µM) or the corresponding mismatched (M) or sense (S) control oligonucleotides (see Table 1) in the same way as described in Example 3. The levels of the mRNA of hCdc6, hMcm2, hCdc45, and the β-actin gene, respectively, were measured by RC-PCR analysis (FIG. 3) as described in Example 3. The antisense oligonucleotides hC6-35a specifically reduced the mRNA level of the target gene hCdc6 (Lane 3), but not the other replication-initiation gene hMcm2 (Lanes 8) or hCdc45 (Lane 13). UT: untreated cells; LP: liposome without oligonucleotides.

Example 6

Figure 4:
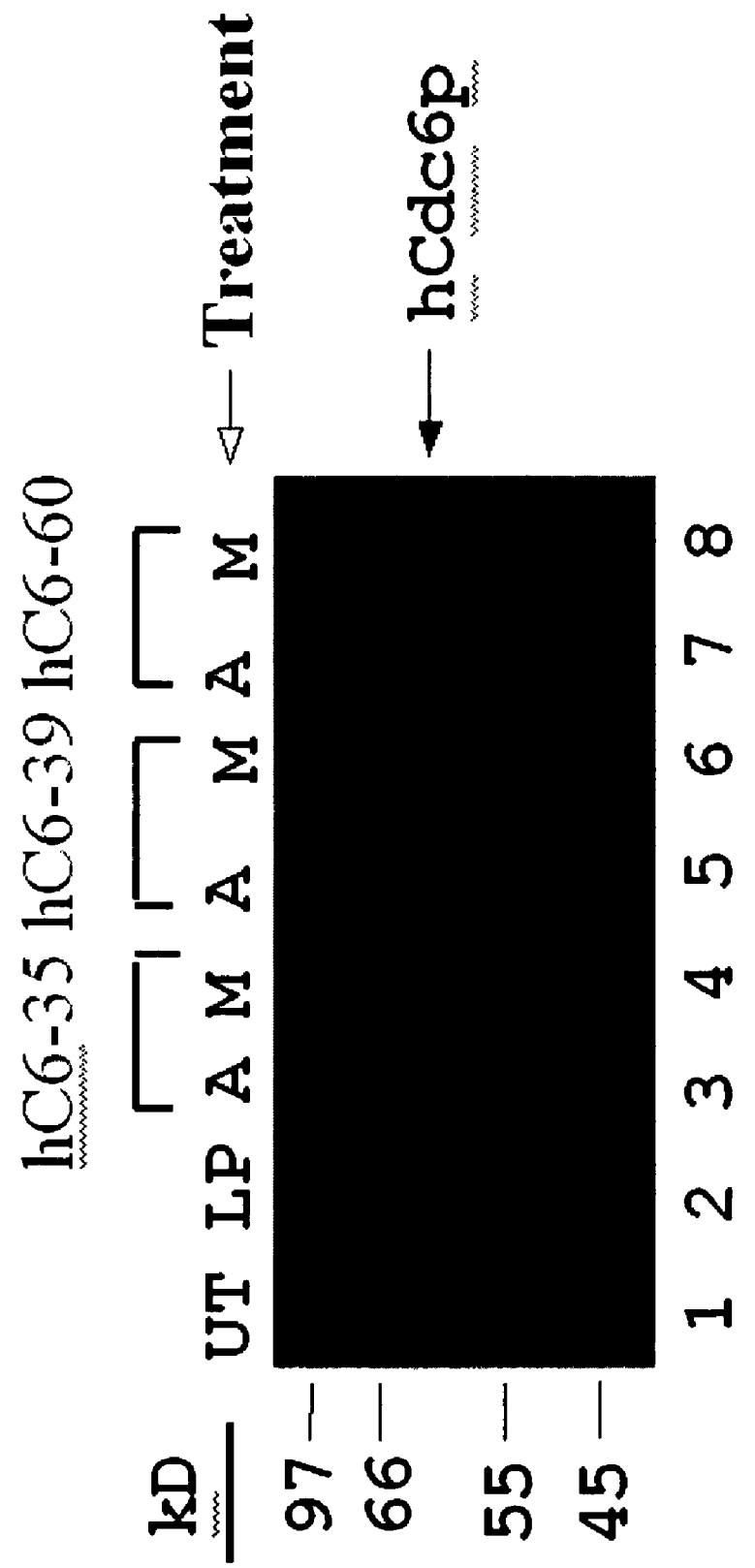
FIG. 4 illustrates the results from Western blotting for hCdc6 in the protein extracts from cells treated with SEQ. ID. Nos. 1, 4, and 6 targeted to hCdc6.

The Antisense Oligonucleotides That Are Targeted to hCdc6 and Have Anti-Cancer Cell Activities Reduced the hCdc6 Protein Level. The Chang's Liver Cancer Cells were treated with the antisense oligonucleotides hC6-35a, hC6-39a, or hC6-60a (0.7 µM) (see Table 1) conjugated with LIPOFECTAMINE-2000™ (1%) in 100 µl of the OPTI-MEM™ medium without serum for 4 hrs. The corresponding mismatched oligonucleotides were used as the negative control. The cells were then grown in regular DMEM containing serum for 1.5 hrs before proteins were extracted and Western blotted with a monoclonal anti-hCdc6 antibody (SANTA CRUZ BIOTECHNOLOGY®) (FIG. 4). UT: untreated cells; LP: treated with liposome without oligonucleotides; A: antisense oligonucleotides; M: mismatched oligonucleotides. Each of the three active antisense oligonucleotides hC6-35a, hC6-39a, and hC6-60a reduced the hCdc6 protein level (Lanes 3, 5 and 7).

Example 7

Figure 5B:
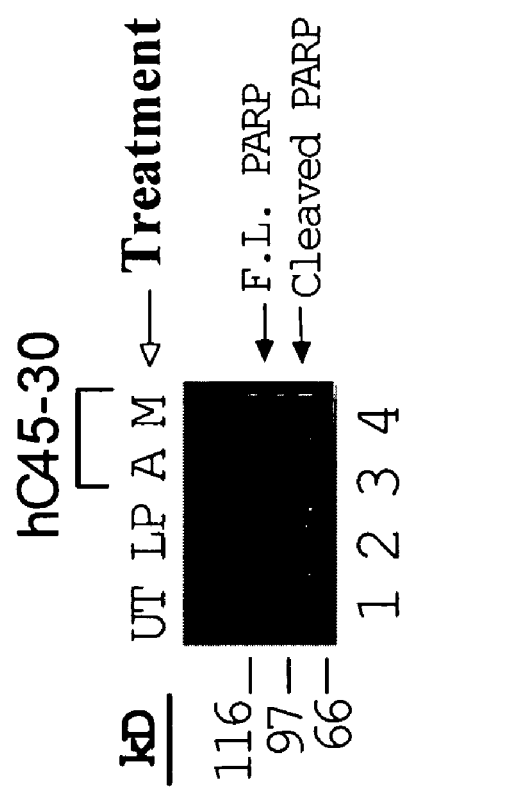
FIG. 5 illustrates the results from Western blotting for Caspase-3 (A) and PARP (B) in the protein extracts from cells treated with SEQ. ID. No. 25 targeted to hCdc45.
Figure 5A:
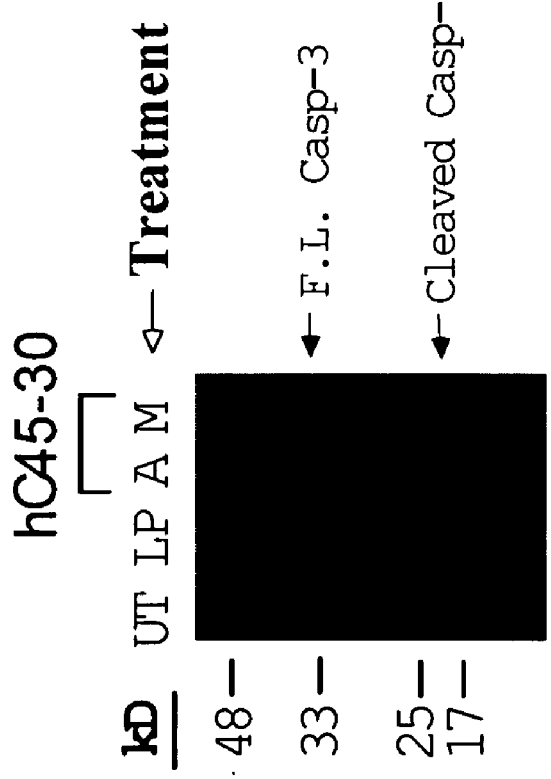

The Antisense Oligonucleotides hC45-30a with Anti-Cancer Cell Activities Induced Activation of Caspase-3 and Cleavage of PARP Indicative of Apoptosis (Programmed Cell Death). The Chang's Liver Cancer Cells were treated with the antisense oligonucleotides hC45-30a (A) (0.7 µM) or the corresponding mismatched (M) control oligonucleotides (see Table 1) in the same way as described in Example 3. Proteins were extracted from the oligonucleotides-treated and control cells and Western blotted with a polyclonal anti-caspase-3 antiserum or a monoclonal anti-PARP antibody (PHARMINGEN®). The antisense oligonucleotides hC45-30a induced activation of caspase-3 (17 kD band; FIG. 5A, Lane 3) and cleavage of caspase-3 substrate PARP (86 kD band; FIG. 5B, Lane 3). Liposome (LP) without oligonucleotides (Lane 2) and the mismatched oligonucleotides (Lane 4) also caused low levels of activation of caspase-3 and PARP cleavage, as they were slightly cytotoxic (see Table 1). UT: untreated cells; F. L. Casp-3: full-length caspase-3.

Example 8

Figure 6:
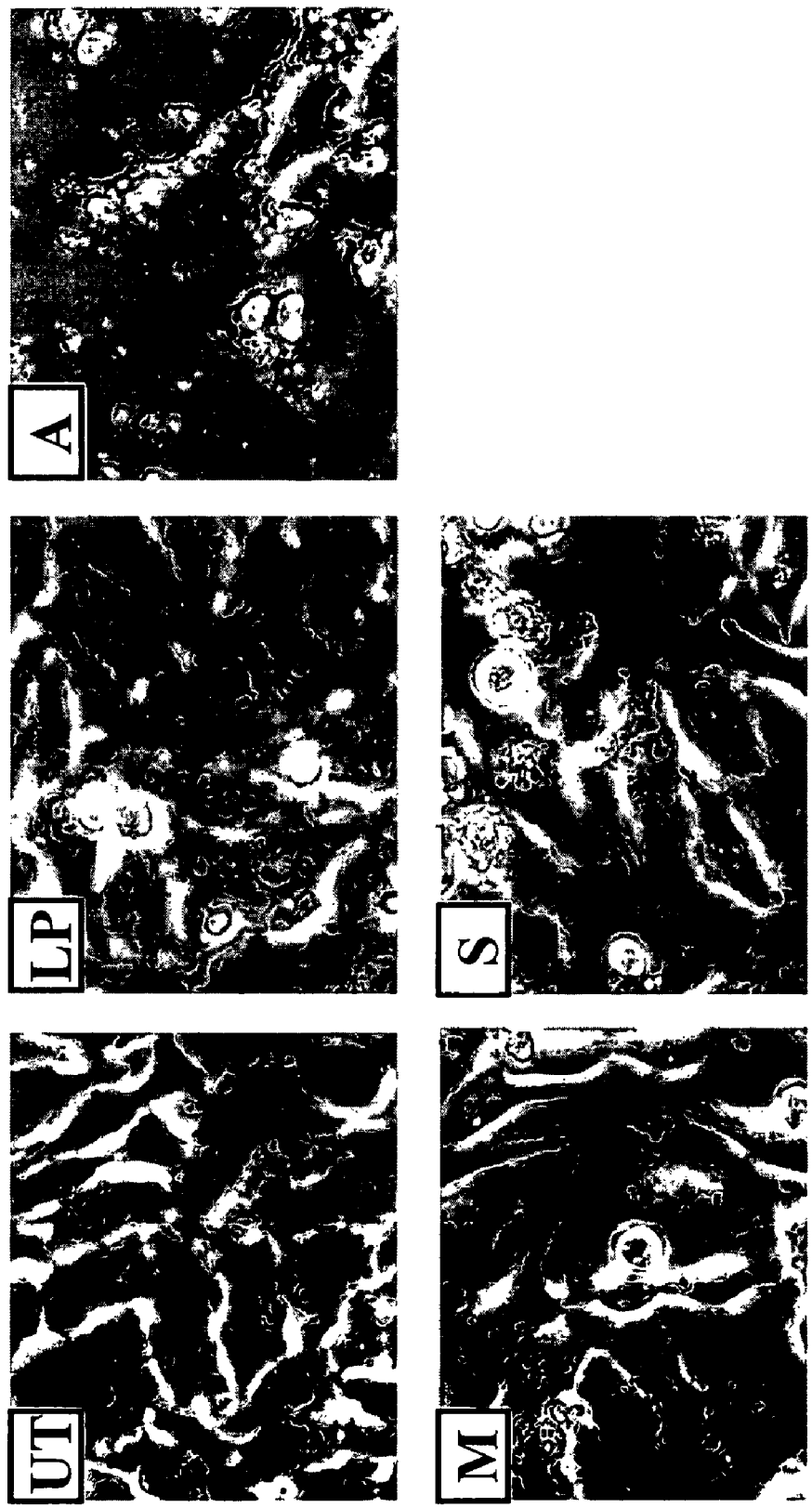
FIG. 6 illustrates the micrographs of the untreated cells and those treated with liposome without oligonucleotides, the antisense oligonucleotide SEQ. ID. No. 16 or the control oligonucleotides SEQ. ID. Nos. 17 and 18.
Figure 7:
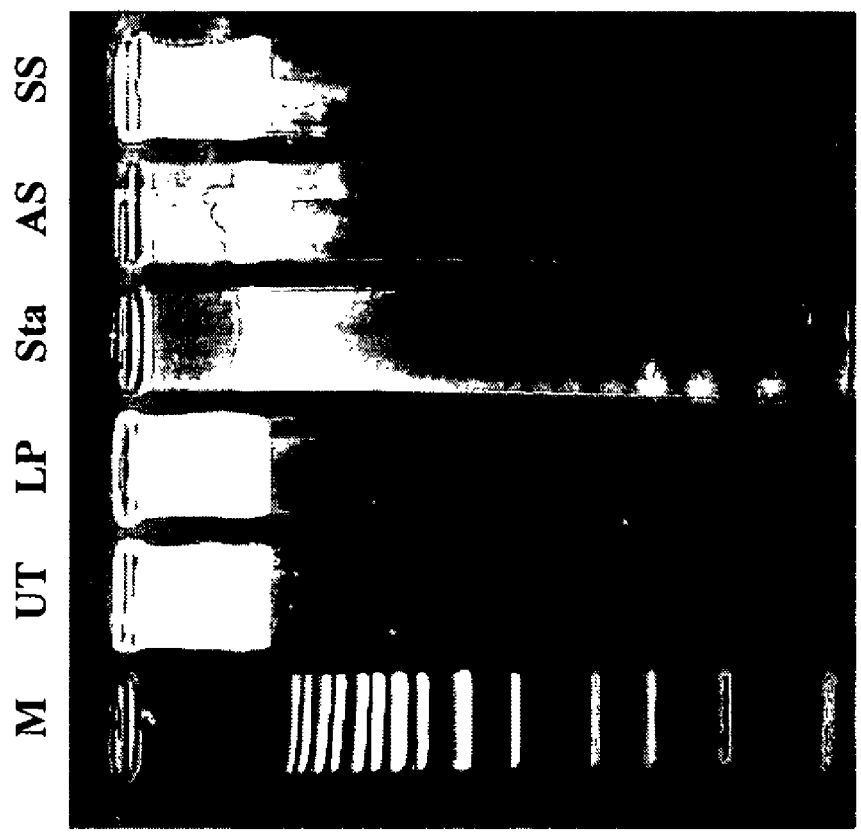
FIG. 7 illustrates the results of DNA fragmentation, which is an indication of apoptotic cell death induced by SEQ. ID. No. 25.
Figure 8:
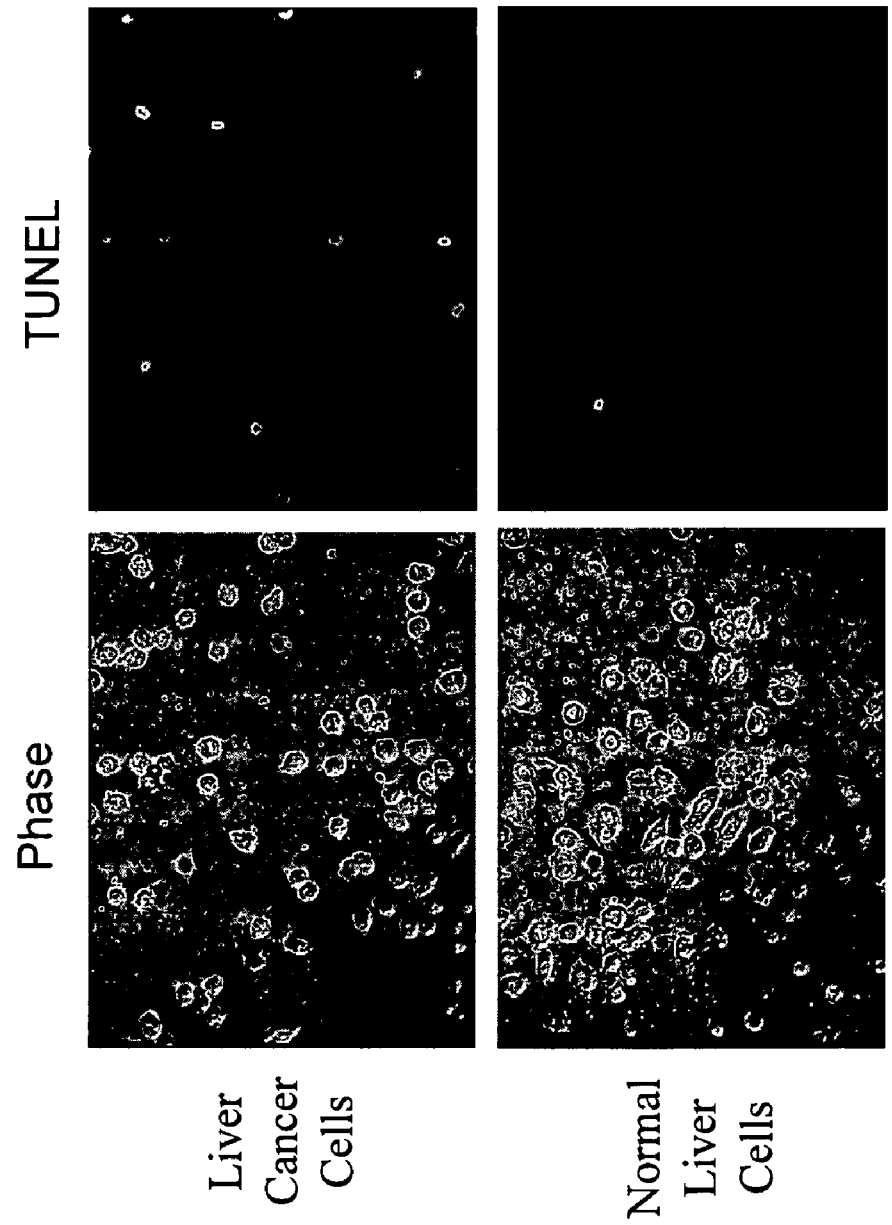
FIG. 8 illustrates the results of DNA fragmentation, as measured by the TUNEL assay, in liver cancer cells, but not in normal liver cells after treatment with SEQ. ID. No. 16.
Figure 9:
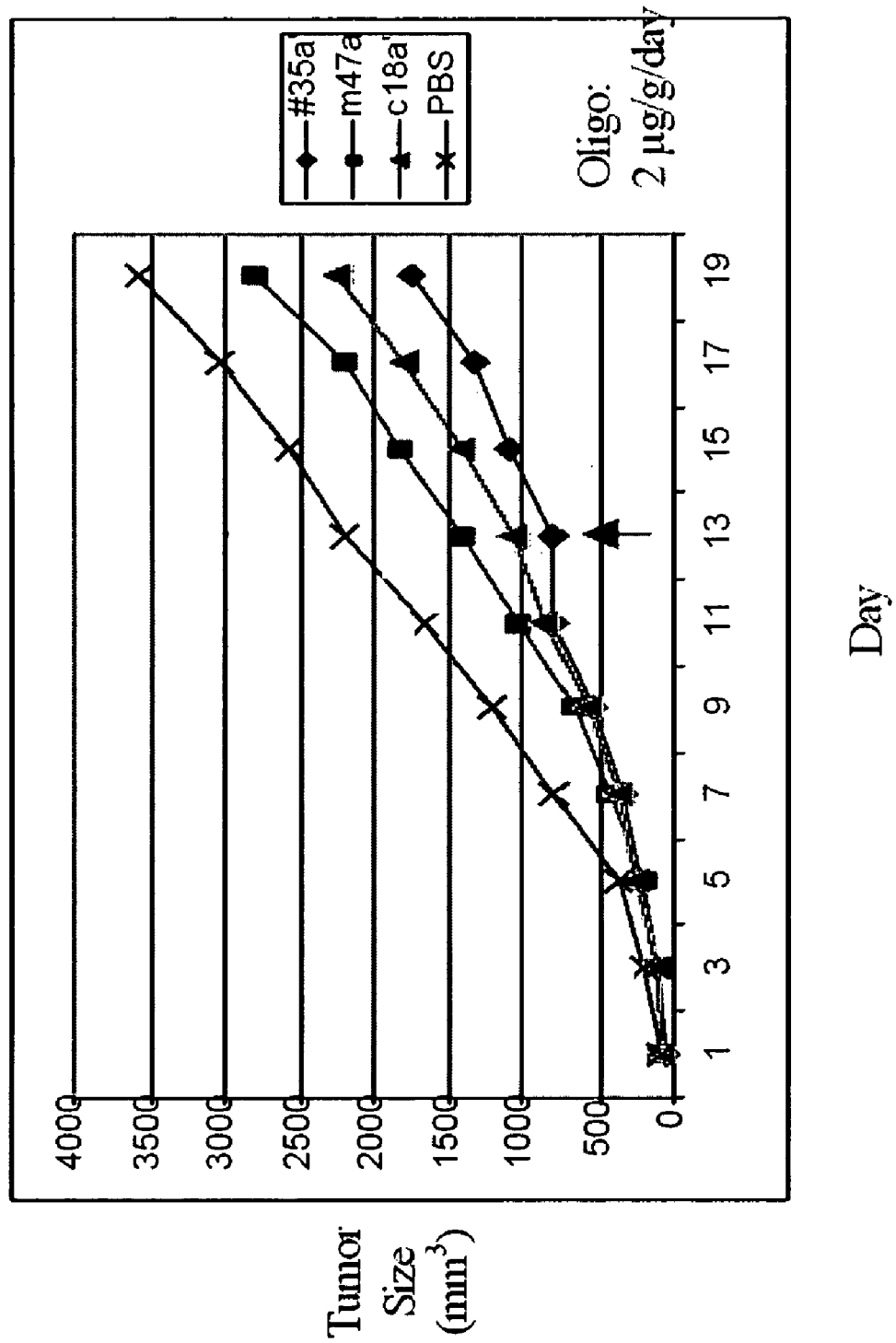
FIG. 9 illustrates the results showing that antisense oligonucleotides Seq. ID. Nos. 1, 16, and 20 reduced human cancer growth in nude mice xenographs.

The Antisense Oligonucleotides hM2-7a Induced Cancer Cell Death. The Chang's Liver Cancer Cells were treated with the antisense oligonucleotides hM2-47a (0.7 µM) or the corresponding mismatched (hM2-47m) or sense (hM2-47s) control oligonucleotides (see Table 1) conjugated with LIPOFECTAMINE Plus™ (2%) in 70 μl of the OPTI-MEM™ medium without serum for 3 hrs. The cells were then grown in regular DMEM containing serum for 2 days before being photographed under an inverted light microscope (FIG. 6). The antisense oligonucleotides hM2-47a induced cell death of most of the cancer cells. UT: untreated cells; LP: liposome without oligonucleotides; A: antisense oligonucleotides; M: mismatched oligonucleotides; S: sense oligonucleotides.

Example 9

The Antisense Oligonucleotides Induced Apoptotic Cell Death. The Chang's Liver Cancer Cells were treated with an antisense oligonucleotides (0.7 μM) or the corresponding sense control oligonucleotides conjugated with LIPOFECTAMINE PLUS™ (2%) in 70 μl of the OPTI-MEM™ medium without serum for 3 hrs. The cells were then grown in regular DMEM containing serum for 4 hours before being harvested for DNA isolation and analysis on an agarose gel. The antisense oligonucleotides induced DNA fragmentation, which is an indication of apoptotic cell death. M: DNA molecular weight markers; UT: untreated cells; LP: liposome without oligonucleotides; Sta: Staurasporine (as a positive control for apoptosis); AS: antisense oligonucleotides; SS: sense control oligonucleotides.

Example 10

The antisense oligonucleotides induced apoptosis in liver cancer cells, but not in normal liver cells. The Chang's Liver Cancer Cells or the L-02 normal liver cells were treated with an antisense oligonucleotides (0.7 μM) conjugated with LIPOFECTAMINE PLUS™ (2%) in 70 μl of the OPTI-MEM™ medium without serum for 3 hrs. The cells were then grown in regular DMEM containing serum for 4 hours before being analyzed by the TUNEL assay for DNA fragmentation, which is an indication of apoptosis. The antisense oligonucleotides induced DNA fragmentation only in lever cancer cells, not in the normal liver cells.

Example 11

The antisense oligonucleotides reduced human cancer growth in nude mice xenographs. Nude mice were inoculated with the HeLa tumor cells (by s.c. injection) and subsequently treated with the antisense oligonucleotides (by i.v. injection; 2 μg/g body weight/day) for 13 days (indicated by the red arrow), three antisense oligonucleotides [hC3-35 (#35a'), hM2-47 (m47a') and hC45-18 (c18a')] significantly reduced tumor growth compared to the control mice injected with the PBS buffer only.

Any reference to documents, acts, materials, devices, articles or the like which has been included in the present specification is solely for the purpose of providing a context for the present claims and are incorporated by reference herein. It is not to be taken as an admission that any or all of these matters form part of the prior art and/or modifications may be made to the invention as shown in the specific embodiments without departing from the spirit or scope of the invention as broadly described. The present embodiments are, therefore, to be considered in all respects as illustrative and not restrictive.

What is claimed is:

1. An antisense oligonucleotide selected from the group consisting of SEQ ID NO:1, SEQ ID NO:4, SEQ ID NO:7, SEQ ID NO:10, SEQ ID NO:13, SEQ ID NO:16, SEQ ID NO:22, and SEQ ID NO:25.

* * * * *

UNITED STATES PATENT AND TRADEMARK OFFICE
CERTIFICATE OF CORRECTION

PATENT NO. : 8,318,922 B2  
APPLICATION NO. : 12/126862  
DATED : November 27, 2012  
INVENTOR(S) : Chun Liang et al.

Page 1 of 1

It is certified that error appears in the above-identified patent and that said Letters Patent is hereby corrected as shown below:

On the Title Page

Item (73), should read:  
(73) Assignee: The Hong Kong University of Science & Technology, Hong Kong (CN)

Signed and Sealed this  
Fifteenth Day of September, 2020

Andrei Iancu  
*Director of the United States Patent and Trademark Office*